United States Patent
Osorio et al.

(10) Patent No.: US 8,246,681 B2
(45) Date of Patent: Aug. 21, 2012

(54) METHODS FOR TREATING A FRACTURED AND/OR DISEASED AND/OR WEAKENED BONE

(75) Inventors: Reynaldo A Osorio, Daly City, CA (US); Marialulu Follmer, Santa Clara, CA (US); Richard W Layne, Palo Alto, CA (US); Ryan P Boucher, San Francisco, CA (US); Karen D Talmadge, Palo Alto, CA (US); Joseph J Basista, Mountain View, CA (US)

(73) Assignee: Kyphon Sarl, Neuchatel (CH)

( * ) Notice: Subject to any disclaimer, the term of this patent is extended or adjusted under 35 U.S.C. 154(b) by 974 days.

(21) Appl. No.: 11/978,271

(22) Filed: Oct. 29, 2007

(65) Prior Publication Data

US 2008/0065087 A1   Mar. 13, 2008

Related U.S. Application Data

(60) Division of application No. 11/789,643, filed on Apr. 25, 2007, which is a division of application No. 10/783,723, filed on Feb. 20, 2004, now abandoned, which is a division of application No. 09/827,260, filed on Apr. 5, 2001, now Pat. No. 6,726,691, said application No. 10/783,723 is a continuation-in-part of application No. 10/346,618, filed on Jan. 17, 2003, now abandoned, which is a division of application No. 09/597,646, filed on Jun. 20, 2000, now Pat. No. 6,716,216, which is a continuation-in-part of application No. 09/134,323, filed on Aug. 14, 1998, now Pat. No. 6,241,734, application No. 11/978,271, which is a continuation-in-part of application No. 10/958,600, filed on Oct. 5, 2004, now abandoned, which is a division of application No. 09/754,451, filed on Jan. 4, 2001, now Pat. No. 6,899,719, which is a continuation of application No. 08/871,114, filed on Jun. 9, 1997, now Pat. No. 6,248,110, which is a continuation-in-part of application No. 08/659,678, filed on Jun. 5, 1996, now Pat. No. 5,827,289, which is a continuation-in-part of application No. 08/485,394, filed on Jun. 7, 1995, now abandoned, which is a continuation-in-part of application No. 08/188,224, filed on Jan. 26, 1994, now abandoned.

(60) Provisional application No. 60/194,685, filed on Apr. 5, 2000.

(51) Int. Cl.
    *A61F 2/44*           (2006.01)
(52) U.S. Cl. ...................................... 623/17.11; 606/93
(58) Field of Classification Search ............ 606/92–94, 606/90, 105; 623/17.11–17.12
    See application file for complete search history.

(56) References Cited

U.S. PATENT DOCUMENTS 1,965,653 A   7/1934   Kennedy
(Continued)

FOREIGN PATENT DOCUMENTS

DE   3736604   11/1989
(Continued)

OTHER PUBLICATIONS

Aebi, M., "The Internal Skeletal Fixation System. A New Treatment of Thoracolumbar Fractures and Other Spinal Disorders", Clinical . Orthop., vol. 227, pp. 30-43 (1988).

(Continued)

*Primary Examiner* — Eduardo C Robert
*Assistant Examiner* — Tara Carter

(57) ABSTRACT

Introduction of a bone filler material into at least a portion of the cancellous bone volume pressurizes the bone filler material and compresses the cancellous bone volume within the bone structure.

14 Claims, 22 Drawing Sheets

U.S. PATENT DOCUMENTS

| | | | |
|---|---|---|---|
| 3,049,125 A | 8/1962 | Kriwkowitsch |
| 3,091,237 A | 5/1963 | Skinner |
| 3,112,743 A | 12/1963 | Cochran et al. |
| 3,626,949 A | 12/1971 | Shute |
| 3,648,294 A | 3/1972 | Shahrestani |
| 3,766,924 A | 10/1973 | Pidgeon |
| 3,779,241 A | 12/1973 | Vennard et al. |
| 3,800,788 A | 4/1974 | White |
| 3,850,176 A | 11/1974 | Gottschalk |
| 3,875,595 A | 4/1975 | Froning |
| 3,889,665 A | 6/1975 | Ling et al. |
| 3,997,138 A | 12/1976 | Crock et al. |
| 4,018,230 A | 4/1977 | Ochiai et al. |
| 4,083,369 A | 4/1978 | Sinnreich |
| 4,205,683 A | 6/1980 | O'Neill |
| 4,274,163 A | 6/1981 | Malcom et al. |
| 4,313,434 A | 2/1982 | Segal |
| 4,327,736 A | 5/1982 | Inoue |
| 4,367,816 A | 1/1983 | Wilkes |
| 4,369,772 A | 1/1983 | Miller |
| 4,399,814 A | 8/1983 | Pratt, Jr. et al. |
| 4,432,358 A | 2/1984 | Fixel |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,494,535 A | 1/1985 | Haig |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,637,396 A | 1/1987 | Cook |
| 4,653,489 A | 3/1987 | Tronzo |
| 4,685,447 A | 8/1987 | Iversen et al. |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,772,287 A | 9/1988 | Ray et al. |
| 4,842,585 A | 6/1989 | Witt |
| 4,878,495 A | 11/1989 | Grayzel |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,909,252 A | 3/1990 | Goldberger |
| 4,932,975 A | 6/1990 | Main et al. |
| 4,969,888 A * | 11/1990 | Scholten et al. ............... 606/94 |
| 4,987,892 A | 1/1991 | Krag et al. |
| 5,002,576 A | 3/1991 | Fuhrmann et al. |
| 5,015,255 A | 5/1991 | Kuslich |
| 5,049,132 A | 9/1991 | Shaffer et al. |
| 5,053,035 A | 10/1991 | McLaren |
| 5,062,845 A | 11/1991 | Kuslich et al. |
| 5,071,435 A | 12/1991 | Fuchs et al. |
| 5,100,390 A | 3/1992 | Lubeck et al. |
| 5,102,413 A | 4/1992 | Poddar |
| 5,108,404 A | 4/1992 | Scholten et al. |
| 5,116,305 A | 5/1992 | Milder et al. |
| 5,127,912 A | 7/1992 | Ray et al. |
| 5,137,512 A | 8/1992 | Burns et al. |
| 5,147,366 A | 9/1992 | Arroyo et al. |
| 5,163,949 A | 11/1992 | Bonutti |
| 5,163,989 A | 11/1992 | Campbell et al. |
| 5,176,638 A | 1/1993 | Don Michael |
| 5,176,683 A | 1/1993 | Kimsey et al. |
| 5,176,692 A | 1/1993 | Wilk et al. |
| 5,254,091 A | 10/1993 | Aliahmad |
| 5,290,306 A | 3/1994 | Trotta et al. |
| 5,295,994 A | 3/1994 | Bonutti |
| 5,303,718 A | 4/1994 | Krajicek |
| 5,330,429 A | 7/1994 | Noguchi et al. |
| 5,331,975 A | 7/1994 | Bonutti |
| 5,359,995 A | 11/1994 | Sewell, Jr. |
| 5,361,752 A | 11/1994 | Moll et al. |
| 5,380,290 A | 1/1995 | Makower et al. |
| 5,383,932 A | 1/1995 | Wilson et al. |
| 5,423,850 A | 6/1995 | Berger |
| 5,425,710 A | 6/1995 | Khair et al. |
| 5,439,447 A | 8/1995 | Miraki |
| 5,441,538 A | 8/1995 | Bonutti |
| 5,445,639 A | 8/1995 | Kuslich et al. |
| 5,454,365 A | 10/1995 | Bonutti |
| 5,467,786 A | 11/1995 | Allen et al. |
| 5,468,245 A | 11/1995 | Vargas, III |
| 5,480,400 A | 1/1996 | Berger |
| 5,514,143 A | 5/1996 | Bonutti et al. |
| 5,514,153 A | 5/1996 | Bonutti |
| 5,522,790 A | 6/1996 | Moll et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,540,711 A | 7/1996 | Kieturakis et al. |
| 5,545,136 A | 8/1996 | Berger |
| 5,545,222 A | 8/1996 | Bonutti |
| 5,549,388 A | 8/1996 | Wilkes |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,601,590 A | 2/1997 | Bonutti et al. |
| 5,681,317 A | 10/1997 | Calderise |
| 5,755,690 A | 5/1998 | Saab |
| 5,772,681 A | 6/1998 | Leoni |
| 5,788,703 A | 8/1998 | Mittelmeier et al. |
| 5,792,044 A | 8/1998 | Foley et al. |
| 5,817,074 A | 10/1998 | Racz |
| 5,827,289 A | 10/1998 | Reiley et al. |
| 5,837,752 A | 11/1998 | Shastri |
| 5,849,014 A | 12/1998 | Mastrorio et al. |
| 5,865,728 A | 2/1999 | Moll et al. |
| 5,893,840 A | 4/1999 | Hull et al. |
| 5,928,162 A | 7/1999 | Giurtino et al. |
| 5,961,499 A | 10/1999 | Bonutti et al. |
| 5,972,015 A | 10/1999 | Scribner et al. |
| 5,976,105 A | 11/1999 | Marcove et al. |
| 6,017,305 A | 1/2000 | Bonutti |
| 6,036,682 A | 3/2000 | Lange et al. |
| 6,036,711 A | 3/2000 | Mozdzierz et al. |
| 6,048,346 A | 4/2000 | Reiley et al. |
| 6,066,154 A | 5/2000 | Reiley et al. |
| 6,117,456 A | 9/2000 | Lee |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,280,456 B1 | 8/2001 | Scribner et al. |
| 6,306,177 B1 | 10/2001 | Felt |
| 6,423,083 B2 | 7/2002 | Reiley et al. |
| 6,440,138 B1 | 8/2002 | Reiley et al. |
| 6,468,279 B1 | 10/2002 | Reo |
| 6,488,653 B1 | 12/2002 | Lombardo |
| 6,582,446 B1 | 6/2003 | Marchosky |
| 6,607,544 B1 | 8/2003 | Boucher et al. |
| 6,852,095 B1 * | 2/2005 | Ray ........................ 604/93.01 |
| 2002/0010472 A1 | 1/2002 | Kuslich et al. |
| 2002/0032447 A1 | 3/2002 | Weikel et al. |
| 2002/0099385 A1 | 7/2002 | Ralph et al. |
| 2003/0050702 A1 | 3/2003 | Berger |
| 2003/0130664 A1 | 7/2003 | Boucher et al. |

FOREIGN PATENT DOCUMENTS

| | | |
|---|---|---|
| EP | 439636 | 5/1912 |
| EP | 0 493789 | 7/1992 |
| GB | 512456 | 9/1939 |
| JP | 8038618 | 2/1996 |
| NL | 9001858 | 3/1992 |
| SU | 906530 | 2/1982 |
| SU | 1148610 | 4/1985 |
| WO | WO 95/03083 | 2/1995 |
| WO | WO 97/28840 | 8/1997 |
| WO | 9856301 | 12/1998 |
| WO | WO 98/56301 | 12/1998 |
| WO | WO 99/62416 | 12/1999 |
| WO | WO 00/09024 | 2/2000 |

OTHER PUBLICATIONS

Blauth, M., "Therapeutic Concept and Result of Operative Treatment in Acute Trauma of the Thoracic and Lumbar Spine: the Hannover Experience," J. of Orthop. Trauma, vol. 1, No. 3, pp. 240-252 (1987).

Campbells' Operative Orthopaedics, A.H. Crenshaw, Ed., 7th ed., Chapter 44, pp. 1653-1663 (1987).

Carlson, "The Use of Methylmehacrylate in Repair of Neoplastic Lesions in Bone," Radiology, vol. 112, pp. 43-46 (Jul. 1974).

Cohen, L., M.D., "Fractures of the Osteoporotic Spine, Pathologic Fractures in Metabolic Bone Disease", The Orthopedic Clinics of N. America. vol. 21:1, Jan. 1990, pp. 153-152.

Daniaux, H., "Technik und Ergebnisse der Transpedikularen Spongiosaplastick Bei Kompressionsbruchen im Lendenwirbelsaulenbereich" Acta Chir. Austr. (Suppl.), vol. 43, pp. 79-80 (1982) (with English Translation).

Daniaux, H., "Transpedikulare Reposition unde erste Spongiosaplastik Bei Wirbelkorperbruchen der Unteren Brust und Lendenwirbelsaule," Unfallchirurg, vol. 89, pp. 197-213 (1986) (with English Translation).

Dick, W., "The 'Fixatuer Interne' as Versatile Implant for Spine Surgery," Spine, vol. 12(9), pp. 882-900 (1987).

Dick, W., "Use of the Actebular Reamer to Harvest Autogenic Bone Graft Material: A Simple Method for Producing Bone Paste," Arch. Orthop. Trauma Surg., vol. 105, pp. 234-238 (1986).

Edeland, H.G., "Open Reduction of Central Compression Fractures of the Tibia Plateau," Acta Orthop. Scand., vol. 47, pp. 686-689 (1976).

Harrington, K., "The Use of Methylmetharcrylate as an Adjunct in the Internal Fixation of Malignant Neoplastic Fracture", The Journal of Bone and Joint Surgery, vol. 54A, No. 8, Dec. 1972; pp. 1665-1676.

Kennedy, W., "Fracture of the Tibia Condyles: A Preliminary Report of Supplementary Fixation with Methylmethacrylate," Clin. Orthop., vol. 143, pp. 153-157 (1978).

Kunec, J.R., et al., Closed Intramedullary Rodding of Patholigic Fractures with Supplemental Cement, Clinical Orthopaedics and Related Research, vol. 188, pp. 183-186 (Sep. 1984).

Ma, Yuan-zhang, "Os Calsis Fracture Treated by Percutaneous Poking Reduction and Internal Fixation," Chinese Medical J., vol. 97, No. 2, pp. 105-110 (1984).

Melton, III, et al.; "Perspective: How Many Women Have Osteoporosis", Journal of Bone and Mineral Research, vol. 7, No. 9, 1992; pp. 1005-1010.

Olerud, S., "Transpedicular Fixation of Toracolumar Vertebral Fractures", Clin. Orthop., vol. 227,pp. 44-51 (1988).

Pentelenyi, T., "First Hungarian Neurosurgical Experiences with 'Fixateur Interne' in the Treatment of Thoraco-Lumbar Spine Injuries," Acta Neurochir. (Wien), vol. 93, pp. 104-109 (1988).

Riggs, B. Lawrence, M.D. et al. Medical Progress, Involutional Osteoporosis:, The New England Journal of Medicine; Jun. 26, 1986; pp. 1676-1686.

Schatzker, J., Operative Orthopaedics, M. Chapman, Ed., 1st ed., Ch. 35, pp. 421-434 (1998).

Scoville, W., "The Use of Acrylic Plastic for Vertebral Replacement or Fixation in Mestastic Disease of the Spine," J. Neurosurg., vol. 27: 274-79 (Sep. 1967).

Silverman, S.L., "The Clinical Consequences of Vertebral Compression Fracture", Bone, 13, S27-S31 (1992).

\* cited by examiner

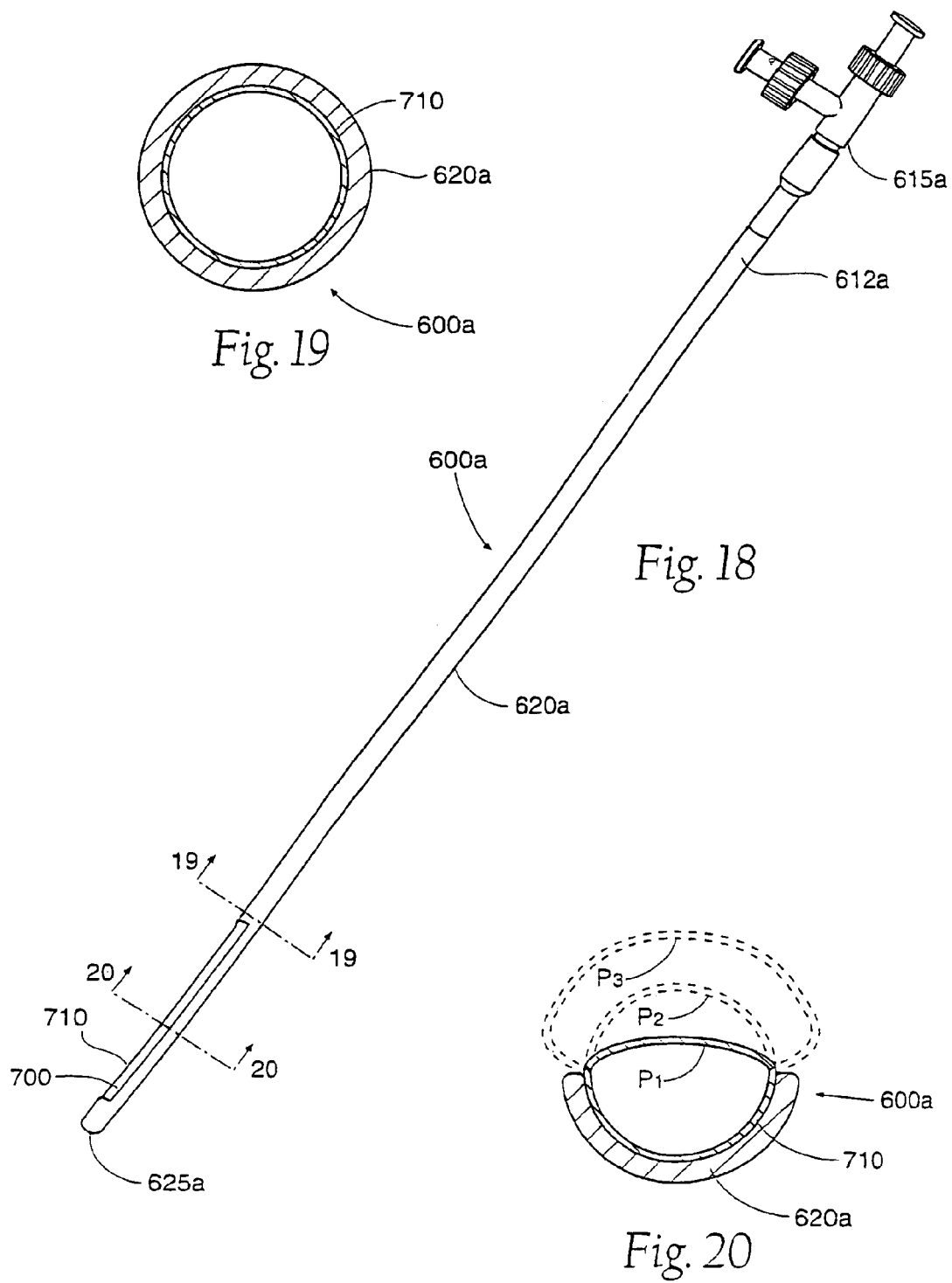

METHODS FOR TREATING A FRACTURED AND/OR DISEASED AND/OR WEAKENED BONE

RELATED APPLICATIONS

This application is a divisional of co-pending U.S. patent application Ser. No. 11/789,643, filed 25 Apr. 2007, and entitled "Methods for Treating Fractured and/or Diseased and/or Weakened Bone," which is a divisional of U.S. patent application Ser. No. 10/783,723, filed 20 Feb. 2004 now abandoned, and entitled "Methods and Devices for Treating Fractured and/or Diseased Bone," which is a divisional of U.S. patent application Ser. No. 09/827,260, filed 5 Apr. 2001 (now U.S. Pat. No. 6,726,691), which claims the benefit of U.S. Provisional Patent Application No. 60/194,685, filed 5 Apr. 2000, and which is also a continuation-in-part of U.S. patent application Ser. No. 10/346,618, filed 17 Jan. 2003 now abandoned, which is a divisional of U.S. patent application Ser. No. 09/597,646, filed 20 Jun. 2000 (now U.S. Pat. No. 6,716,216), which is a continuation-in-part of U.S. patent application Ser. No. 09/134,323, filed 14 Aug. 1998 (now U.S. Pat. No. 6,241,734), each of which is incorporated herein by reference. This application is also a continuation-in-part of U.S. patent application Ser. No. 10/958,600, filed 5 Oct. 2004 now abandoned, and entitled "Systems and Methods for Treating Fractured or Diseased Bone Using Expandable Bodies," which is a divisional of U.S. patent application Ser. No. 09/754,451, filed 4 Jan. 2001 (now U.S. Pat. No. 6,899,719), which is a continuation of U.S. patent application Ser. No. 08/871,114, filed 9 Jun. 1997 (now U.S. Pat. No. 6,248,110), which is a continuation-in-part of U.S. patent application Ser. No. 08/659,678, filed 5 Jun. 1996 (now U.S. Pat. No. 5,827,289); which is a continuation-in-part of U.S. patent application Ser. No. 08/485,394, filed 7 Jun. 1995 (Abandoned), which is a continuation-in-part of U.S. patent application Ser. No. 08/188,224, filed 26 Jan. 1994 (Abandoned), each of which is incorporated herein by reference.

BACKGROUND OF THE INVENTION

1. Field of the Invention

The present invention relates to devices and methods for treating fractured and/or diseased bone. More specifically, the present invention relates to devices and methods for repairing, reinforcing and/or treating fractured and/or diseased bone using various devices, including cavity-forming devices.

2. Description of the Background

Normal healthy bone is composed of a framework made of proteins, collagen and calcium salts. Healthy bone is typically strong enough to withstand the various stresses experienced by an individual during his or her normal daily activities, and can normally withstand much greater stresses for varying lengths of time before failing. However, osteoporosis or a host of other diseases, including such diseases as breast cancer, hemangiomas, osteolytic metastases or spinal myeloma lesions, as well as the long term excessive use of alcohol, tobacco and/or various drugs, can affect and significantly weaken healthy bone over time. If unchecked, such factors can degrade bone strength to a point where the bone is especially prone to fracture, collapse and/or is unable to withstand even normal daily stresses.

Unfortunately, losses in bone strength are often difficult to discover until bone integrity has already been seriously compromised. For instance, the effects of osteoporosis are often not discovered until after a bone fracture has already occurred, at which time much of the patient's overall bone strength has typically weakened to dangerous levels. Moreover, as most bone development occurs primarily during childhood and early adulthood, long-term losses in bone strength are typically irreversible. In addition, many bone diseases, including osteoporosis, cancer, and other bone-related disorders, are not routinely curable at our current stage of medical development.

For many individuals in our aging world population, undiagnosed and/or untreatable bone strength losses have already weakened these individuals' bones to a point that even normal daily activities pose a significant threat of fracture. For example, when the bones of the spine are sufficiently weakened, the compressive forces in the spine can often cause fracture and/or deformation of the vertebral bodies. For sufficiently weakened bone, even normal daily activities like walking down steps or carrying groceries can cause a collapse of one or more spinal bones, much like a piece of chalk collapses under the compressive weight of a human foot. A fracture of the vertebral body in this manner is typically referred to as a vertebral compression fracture. Researchers estimate that at least 25 percent of all women, and a somewhat smaller percentage of men, over the age of 50 will suffer one or more vertebral compression fractures due to osteoporosis alone. In the United States, it is estimated that over 700,000 vertebral compression fractures occur each year, over 200,000 of which require some form of hospitalization. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Until recently, treatment options for vertebral compression fractures, as well as other serious fractures and/or losses in bone strength, were extremely limited—mainly pain management with strong oral or intravenous medications, reduced activity, bracing and/or radiation therapy, all with mediocre results. Because patients with these problems are typically older, and often suffer from various other significant health complications, many of these individuals are unable to tolerate invasive surgery. In addition, to curb further loss of bone strength, many patients are given hormones and/or vitamin/mineral supplements—again with mediocre results and often with significant side effects.

Over the past decade, a technique called vertebroplasty has been introduced into the United States. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

While vertebroplasty has been shown to reduce some pain associated with vertebral compression fractures, this procedure has certain inherent drawbacks. The most significant danger associated with vertebroplasty is the inability of the practitioner to control the flow of liquid bone cement during injection into a vertebral body. Although the location and flow patterns of the cement can be monitored by CT scanning or x-ray fluoroscopy, once the liquid cement exits the injection needle, it naturally follows the path of least resistance within the bone, which is often through the cracks and/or gaps in the cancellous and/or cortical bone. Moreover, because the cancellous bone resists the injection of the bone cement and small diameter needles are typically used in vertebroplasty procedures, extremely high pressures are required to force the bone cement through the needle and into the vertebral body. Bone cement, which is viscous, is difficult to inject through small diameter needles, and thus many practitioners choose to "thin out" the cement mixture to improve cement injection, which ultimately exacerbates the leakage problems. In a recent study where 37 patients with bone metastases or multiple myeloma were treated with vertebroplasty, 72.5% of the procedures resulted in leakage of the cement outside the vertebral body. Cortet B. et al., Percutaneous Vertebroplasty in Patients With Osteolytic Metastases or Multiple Myeloma (1998). Moreover, where the practitioner attempts to "thin out" the cement by adding additional liquid monomer to the cement mix, the amount of unpolymerized or "free" monomer increases, which can ultimately be toxic to the patient.

Another drawback of vertebroplasty is due to the inability to visualize (using CT scanning or x-ray fluoroscopy) the various venous and other soft tissue structures existent within the vertebra. While the position of the needle within the vertebral body is typically visualized, the location of the venous structures within the vertebral body are not. Accordingly, a small diameter vertebroplasty needle can easily be accidentally positioned within a vein in the vertebral body, and liquid cement pumped directly into the venous system, where the cement easily passes out the anterior and/or posterior walls of the vertebrae through the anterior external venous plexus or the basivertebral vein.

Another significant drawback inherent in vertebroplasty is the inability of this procedure to restore the vertebral body to a pre-fractured condition prior to the injection of the reinforcing material. Because the bone is fractured and/or deformed, and not repositioned prior to the injection of cement, vertebroplasty essentially "freezes" the bone in its fractured condition. Moreover, it is highly unlikely that a traditional vertebroplasty procedure could be capable of restoring significant pre-fracture anatomy—because bone cement flows towards the path of least resistance, any en-masse movement of the cortical bone would likely create gaps in the interior and/or walls of the vertebral body through which the bone cement would then immediately flow.

A more recently developed procedure for treating fractures such as vertebral compression fractures and other bone-related disorders is known as Kyphoplasty™. See, for example, U.S. Pat. Nos. 4,969,888 and 5,108,404. In Kyphoplasty, an expandable body is inserted through a small opening in the fractured or weakened bone, and then expanded within the bone. This procedure compresses the cancellous bone, and desirably moves the fractured bone to its pre-fractured orientation, creating a cavity within the bone that can be filled with a settable material such as cement or any number of synthetic bone substitutes. In effect, the procedure "sets" the bone at or near its pre-fracture position and creates an internal "cast," protecting the bone from further fracture and/or collapse. This procedure is of course suitable for use in various other bones as well.

While Kyphoplasty can restore bones to a pre-fractured condition, and injected bone filler is less likely to leak out of the vertebral body during a Kyphoplasty procedure, Kyphoplasty requires a greater number of surgical tools than a vertebroplasty procedure, at an increased cost. Moreover, Kyphoplasty tools are typically larger in diameter than vertebroplasty tools, and thus require larger incisions and are generally more invasive.

SUMMARY OF THE INVENTION

The present invention overcomes many of the problems and disadvantages associated with current strategies and designs in medical procedures to repair, reinforce and/or treat weakened, diseased and/or fractured bone.

One aspect of the invention provides a method comprising compressing at least a portion of a cancellous bone volume within a bone structure, e.g., a vertebral body by injecting a bone filler material into the cancellous bone volume.

In one embodiment, the method comprises moving fractured cortical bone of the bone structure by injecting bone filler material into the cancellous bone volume. The method includes moving fractured cortical bone to a pre-fractured position.

The bone filler material can comprise, e.g., at least one of a bone filler, a bone cement, a synthetic bone substitute, a bone biomaterial, a hydroxyapatite material, a bone mineral material, a thixotropic material, a curable bio-material, allograft tissue, and autograft tissue.

Other objects, advantages, and embodiments of the invention are set forth in part in the description which follows, and in part, will be obvious from this description, or may be learned from the practice of the invention.

BRIEF DESCRIPTION OF THE DRAWINGS

FIG. 18 is a side view of a cavity-forming device constructed in accordance with another alternate embodiment of the present invention;

FIG. 19 is a cross-sectional view of the cavity-forming device of FIG. 18, taken along line 19-19; and FIG. 20 is a cross-sectional view of the cavity-forming device of FIG. 18, taken along line 20-20.

DESCRIPTION OF THE INVENTION

As embodied and broadly described herein, the present invention is directed to surgical methods for repairing, reinforcing and/or treating weakened, diseased and/or fractured bone. The present invention is further directed to various devices for facilitating such surgical methods.

Figure 1:
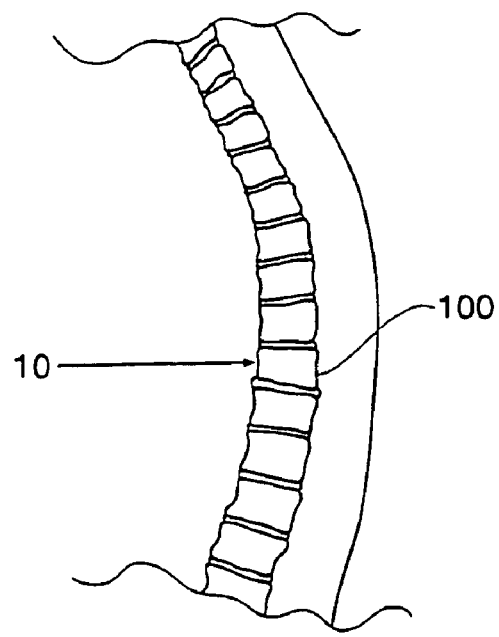
FIG. 1 is a diagram of a spine with a compression fracture in one vertebrae.
Figure 3:
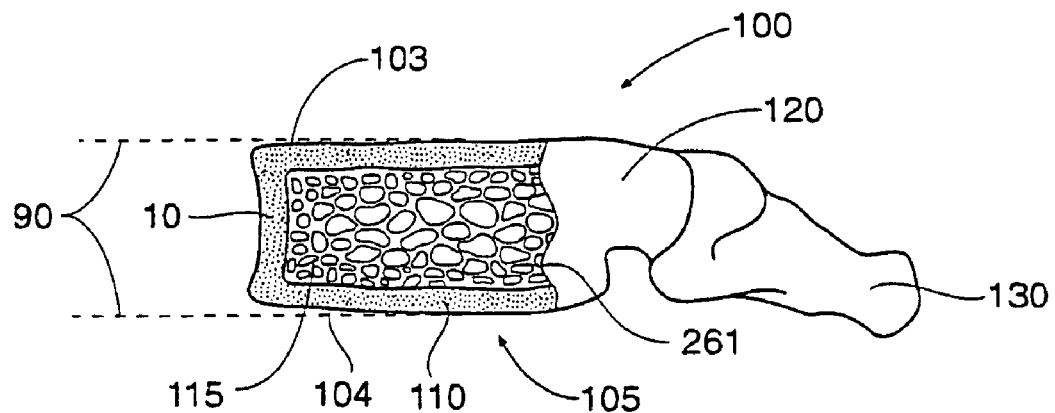
FIG. 3 is a lateral view, partially broken away and in section, of a lumbar vertebra depicting a compression fracture.

FIG. 1 depicts a typical human spine 1, in which a compression fracture 10 has occurred in a lumbar vertebra 100. As best shown in FIG. 3, vertebra 100 has fractured, with the top and bottom plates 103 and 104 depressing generally towards the anterior wall 10 of the vertebra 100 and away from their pre-fracture, normally parallel orientation (indicated generally as parallel lines 90).

Figure 4:
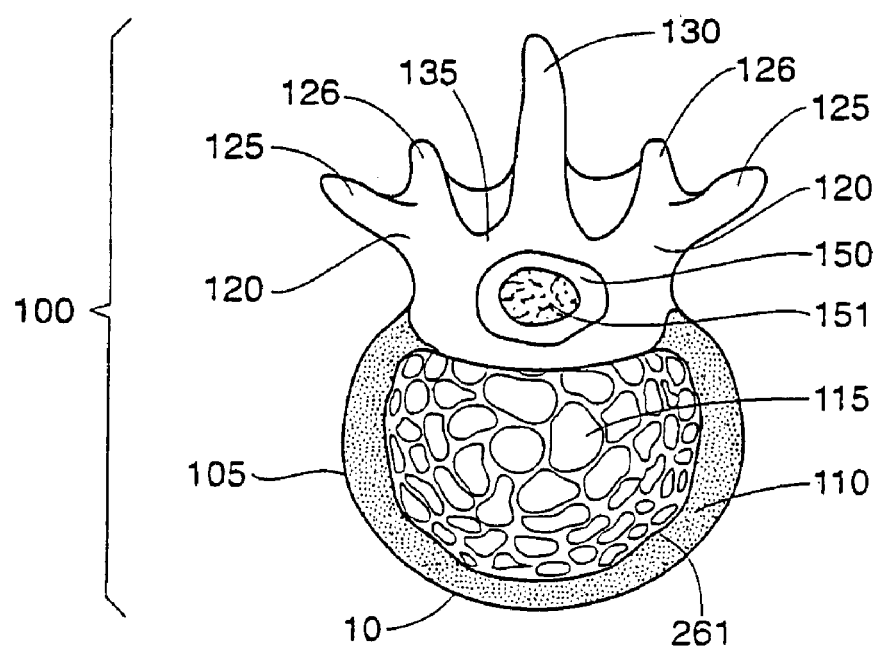
FIG. 4 is a coronal view of a lumbar vertebra.

FIG. 4 depicts a coronal (top) view of the vertebra of FIG. 3. Vertebra 100 includes a vertebral body 105, which extends on the anterior (i.e. front or chest) side of the vertebra 100. Vertebral body 105 is approximately the shape of an oval disk, with an anterior wall 10 and a posterior wall 261. The geometry of the vertebral body 105 is generally symmetric. Vertebral body 105 includes an exterior formed from compact cortical bone 110. The cortical bone 110 encloses an interior volume of reticulated cancellous, or spongy, bone 115 (also called medullar bone or trabecular bone).

The spinal canal 150 is located on the posterior (i.e. back) side of each vertebra 100. The spinal cord 151 passes through the spinal canal 150. A vertebral arch 135 surrounds the spinal canal 150. Left and right pedicles 120 of the vertebral arch 135 adjoin the vertebral body 105. The spinous process 130 extends from the posterior of the vertebral arch 135, as do the left and right transverse processes 125 and the mamillary processes 126.

Figure 2:
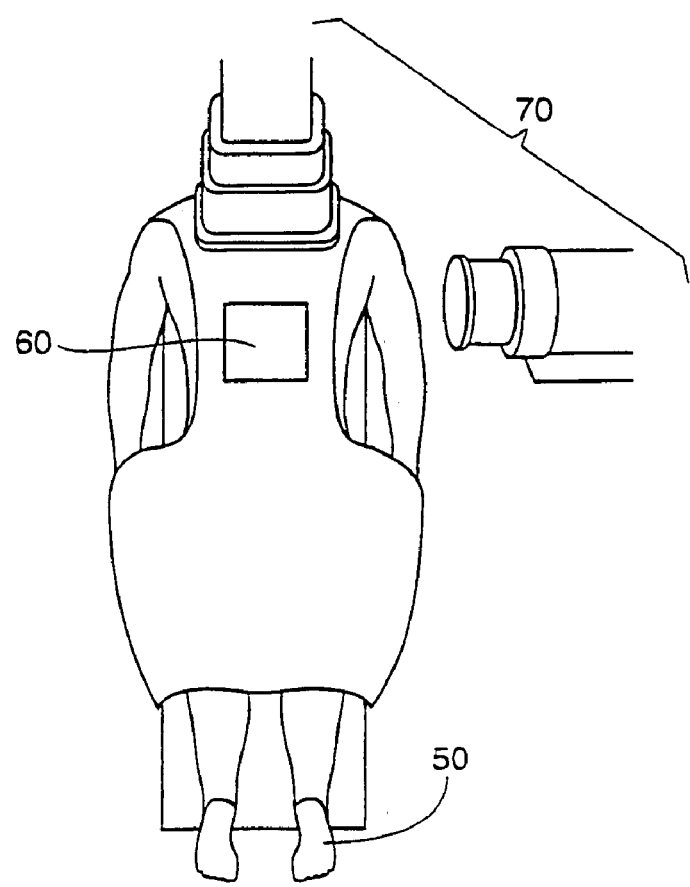
FIG. 2 is a diagram of a patient about to undergo surgery.

FIG. 2 depicts a patient 50 prepared for disclosed methods of the present invention. These procedures can be performed on an outpatient or inpatient basis by a medical professional properly trained and qualified to perform the disclosed procedures. Desirably, the patient will be placed under general or local anesthetic for the duration of the surgical procedures.

In one embodiment of the present invention, a surgical method comprises inserting an insertion device 350 (see FIG. 5A) percutaneously into the bone, such as a fractured vertebral body 105 through, preferably, a targeted area of the back, depicted as 60 in FIG. 2. The insertion device 350 may be any type and size of hollow instrument, preferably having a sharp end. In one preferred embodiment, the insertion device 350 comprises a hollow needle of approximately eleven gauge diameter. An eleven gauge needle is preferred for the procedure because it incorporates a hollow lumen of sufficient size to permit the passage of various instruments and materials, yet the overall size of the needle is small enough to minimize bone and tissue damage in the patient. It should be understood, however, that various other size needle assemblies, including needles of six to 14 gage, could be used with the devices and methods of the present invention, with varying results. In addition, various other access instruments, such as those described in U.S. Pat. Nos. 4,969,888, 5,108,404, 5,827,289, 5,972,015, 6,048,346 and 6,066,154, each of which are incorporated herein by reference, could be used in accordance with the teachings of the present invention, with varying results.

Figure 5A:
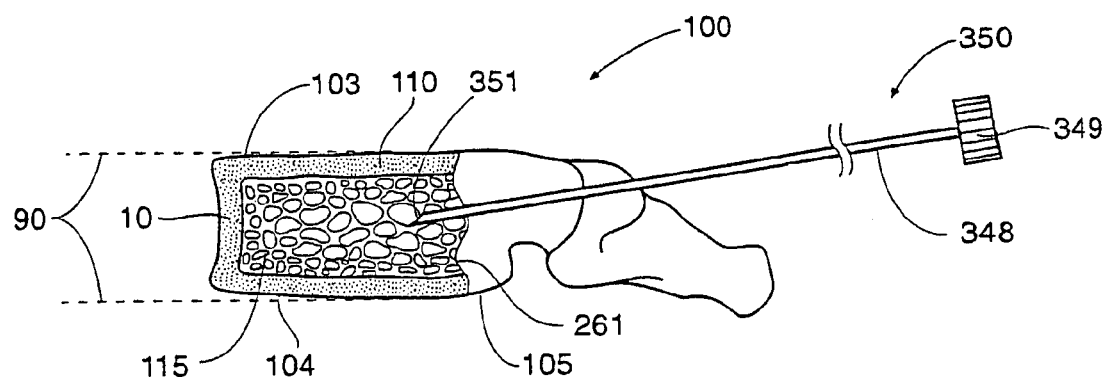
FIG. 5A is a lateral view of a lumbar vertebra depicting a spinal needle inserted into the vertebral body.

The insertion device 350 is preferably comprised of a strong, non-reactive, and medical grade material such as surgical steel. If desired, the insertion device 350 is attached to a manipulating assembly which is comprised of a non-reactive and medical grade material including, but not limited to, acrylonitrile-butadiene-styrene (ABS), polyethylene, polypropylene, polyurethane, Teflon, or surgical steel. FIG. 5A depicts a commercially available needle assembly typically used with various embodiments of the present invention, which are further described below.

As shown in FIG. 5A, an insertion device 350, such as an eleven gauge biopsy needle (commercially available from Becton Dickinson & Co of Franklin Lakes, N.J.) can be inserted through soft tissues of the back and into the vertebral body 105. Generally, the approach for such a procedure will be transpedicular, although various other approaches, including lateral, extrapedicular and/or anterior approaches, could be used, depending upon the level treated and/or intervening anatomical features well known to those of ordinary skill in the art. In one embodiment, the device 350 comprises a needle body 348 and a stylet 349, as is well known in the art. During insertion of the device 350, the location of the device 350 is desirably monitored using visualization equipment such as real-time X-Ray, CT scanning equipment 70 (see FIG. 2), MRI, or any other monitoring equipment commonly used by those of skill in the art, including computer aided guidance and mapping equipment such as the systems commercially available from BrainLab Corporation or General Electric Corporation.

Figure 5B:
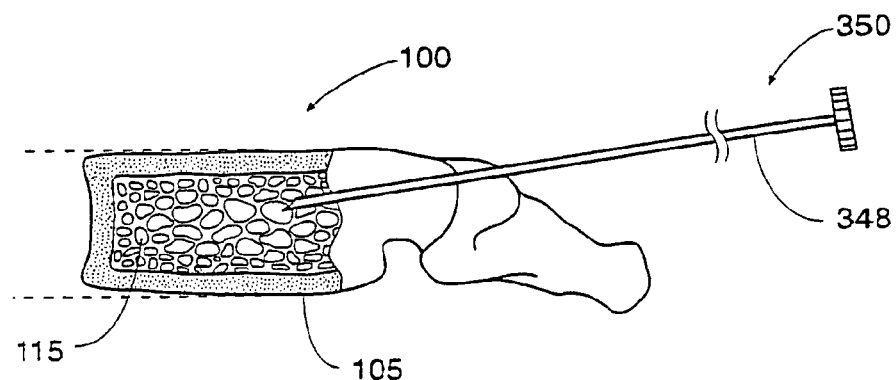
FIG. 5B is a lateral view of the lumbar vertebra of FIG. 5A, with the stylet removed from the spinal needle.
Figure 5C:
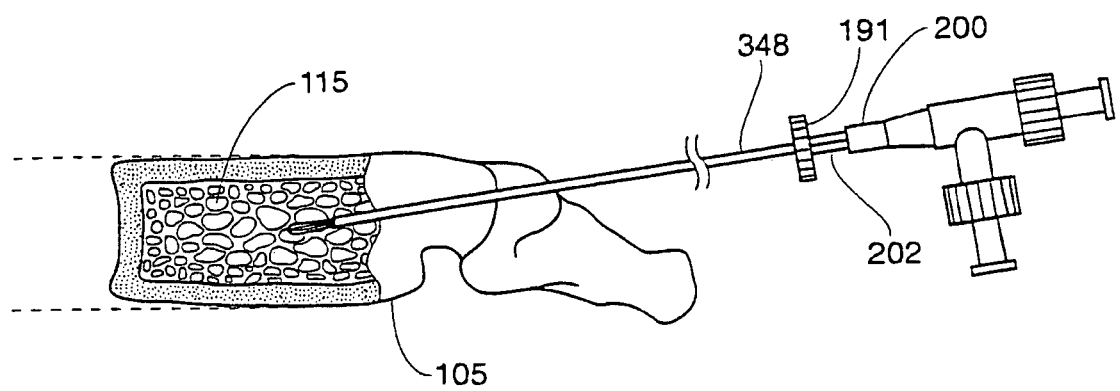
FIG. 5C is a lateral view of the lumbar vertebra of FIG. 5B, with a cavity-forming device constructed in accordance with one embodiment of the present invention inserted into the vertebral body.
Figure 5D:
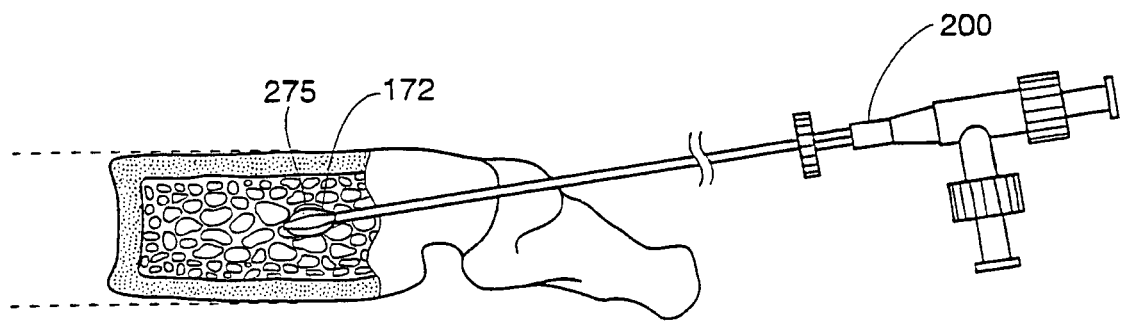
FIG. 5D is a lateral view of the lumbar vertebra of FIG. 5C, with the cavity-forming device inflated.
Figure 5E:
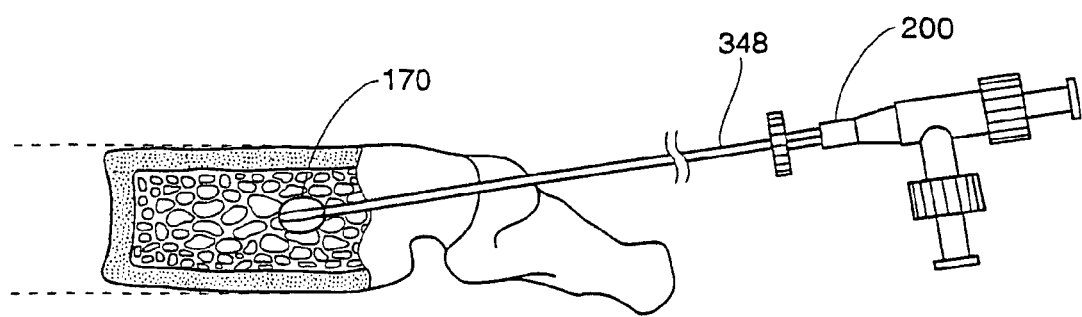
FIG. 5E is a lateral view of the lumbar vertebra of FIG. 5D, with the cavity-forming device deflated.
Figure 5F:
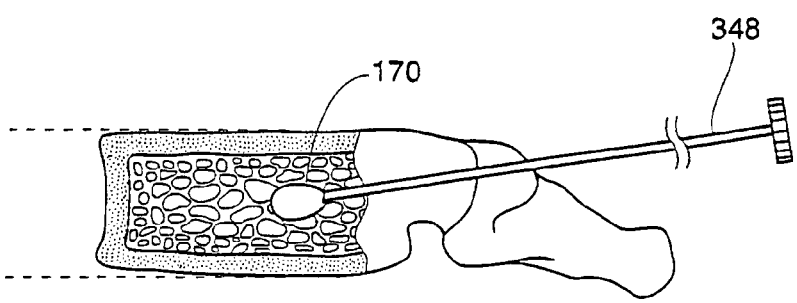
FIG. 5F is a lateral view of the lumbar vertebra of FIG. 5E, with the cavity-forming device removed from the vertebral body.
Figure 5G:
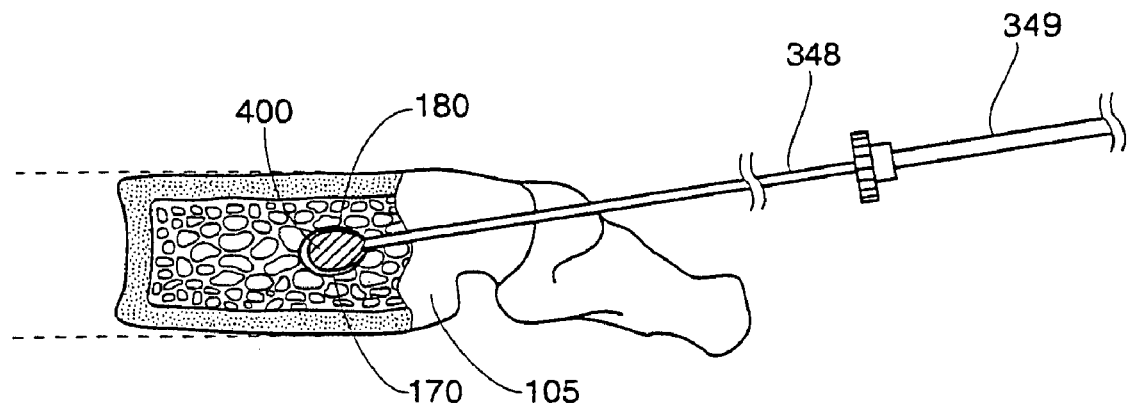
FIG. 5G is a lateral view of the lumbar vertebra of FIG. 5F, with a bone filler injected into the vertebral body.
Figure 5H:
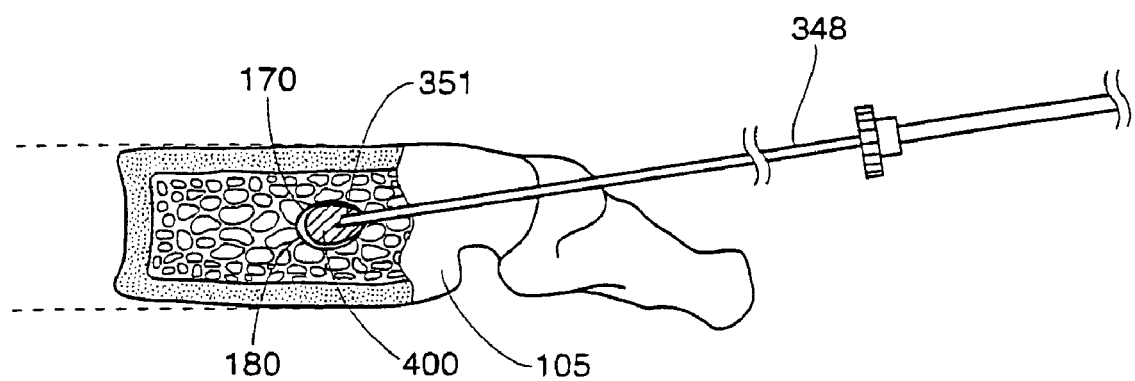
FIG. 5H is a lateral view of the lumbar vertebra of FIG. 5G, with the spinal needle advanced into the cavity.

In one preferred embodiment, the distal end 351 of the insertion device 350 is positioned in the vertebral body 105, preferably at a location towards the posterior side of the vertebral body 105. If desired, the distal end 351 could be positioned in various locations throughout the vertebral body 105, including towards the anterior side. Once in position, the stylet 349 of the insertion device 350 may be removed, see FIG. 5B, and a cavity-forming device 200 may be inserted through the shaft 348 and into the vertebral body 105. See FIG. 5C. The cavity-forming device 200, which is desirably comprised of a biologically compatible and medically acceptable material, can be a small mechanical tamp, reamer, hole punch, balloon catheter (as described below) or any appropriate device which is capable of displacing cancellous bone. Once the cavity-forming device is positioned within the vertebral body 105, it is used to displace cancellous bone 115, thereby creating a cavity 170. See FIG. 5F.

Figure 9:
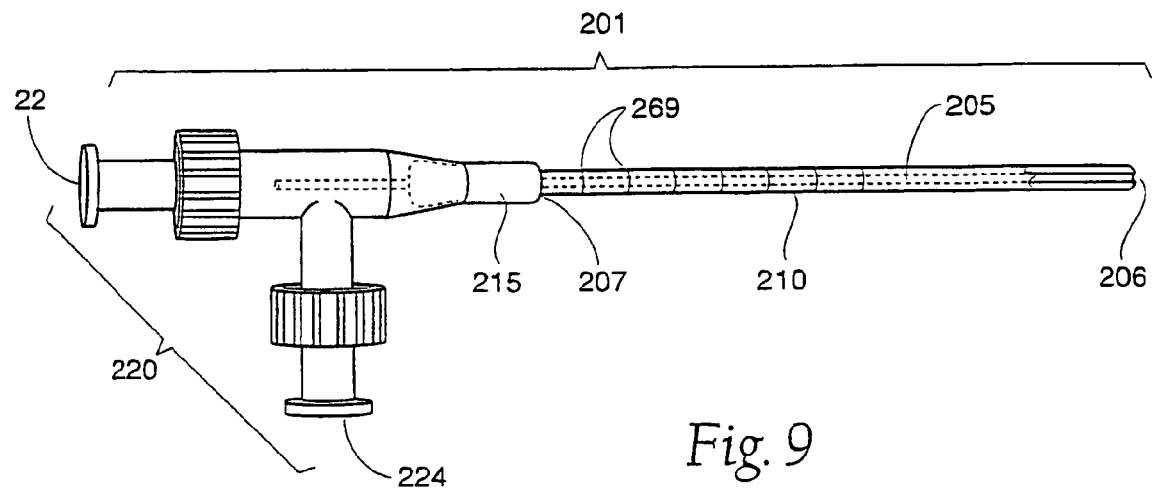
FIG. 9 is a side view of a cavity-forming device constructed in accordance with one embodiment of the present invention.
Figure 10:
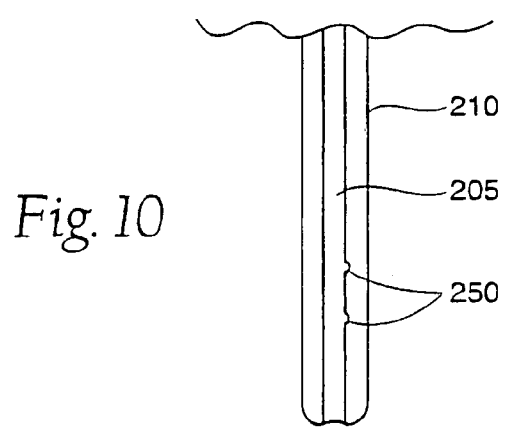
FIG. 10 is a close-up view of the distal end of a cavity-forming device of FIG. 9.

In one embodiment, shown in FIGS. 9 and 10, the cavity-forming device comprises a balloon catheter 200. The balloon catheter 200 desirably extends across at least 20% of the vertebral body, but could extend greater or lesser amounts, depending upon the desired size of the cavity to be produced. In this embodiment, as the balloon catheter 201 is expanded, cancellous bone is displaced generally outward from the cavity 170 in a controlled manner, desirably forming a compressed-bone region 172 around a substantial portion of the outer periphery of the cavity 170.

The balloon catheter 200, which will be described in more detail below, is sized or folded to fit through the hollow interior of the shaft 348 and into a vertebral body 105. Once in a desired position within the vertebral body 105, the balloon catheter 190 is filled with a pressurized filling medium 275 appropriate for use in medical applications including, but not limited to, air, nitrogen, saline or water. See FIGS. 5D and 11. In a preferred embodiment, the filling medium 275 is a radiopaque fluid (such as Conray® fluid available commercially from Mallinkrodt, Inc., of St. Louis, Mo.), which allows the physician to visualize the catheter 190 during inflation. If desired, alternate ways of expanding the catheter, including mechanical expanders, jacks, expanding springs and/or expanding/foaming agents, could be used, with varying results.

In one embodiment, the catheter 201 is expanded to any appropriate volume which creates a cavity 170 within the vertebral body 105. In a preferred embodiment, the catheter 201 is expanded to at least 0.20 cc in volume, but could be expanded to significantly greater sizes, such as 1, 2, 4, 6 or 8 cc, depending upon bone quality and density. After cavity creation, the catheter 201 is deflated (see FIG. 5E) and removed from the vertebral body 105 and shaft 348 (see FIG. 5F). Bone filler 180 is introduced through the shaft 348 and into the vertebral body 105 using any type of plunger, extruder and/or feed line assembly 349 compatible with the needle body 348. Once injection of bone filler is complete, the shaft 348 can be withdrawn.

If desired, a portion of the balloon catheter 201 could be temporarily or permanently left within a vertebral body 105. For example, after cavity formation and removal of the inflation medium, the deflated expanded section of the balloon catheter 201 could be refilled with bone filler 180 and left within the vertebral body 105. Alternatively, the inflation medium 275 could comprise bone filler 180. After the balloon catheter 201 is filled with such an inflation medium, at least a portion of the catheter 201 could be left permanently within the cavity 170. In an alternate embodiment, the catheter 201 which is intended to remain with the cavity 170 could comprise a bio-absorbable material and/or fabric/mesh material as the expandable structure.

In creating the cavity 170, the inflation of the catheter 201 causes the expandable material 210 to press against the cancellous bone 115 which may form a compressed bone region or "shell" 172 along much of the periphery of the cavity 170. This shell 172 will desirably inhibit or prevent bone filler 180 from exiting the cavity 170, thereby inhibiting extravazation of the bone filler and/or facilitating pressurization of the bone filler 180, if desired, within the cavity. As the pressure in the cavity 170 increases, the walls of the cavity 170 will desirably be forced further outward by the bone filler 180, compressing additional cancellous bone within the vertebral body 105 and/or increasing the size of the cavity 170. If sufficient pressure is available, and integrity of the shell 172 can be maintained without significant leakage of bone filler 180, pressures capable of moving fractured cortical bone can be developed.

In one embodiment of the present invention, after cavity formation, an amount of a material, such as a bone filler 180, is introduced through the shaft 348 into the vertebral body 105 under low pressure. The amount of bone filler will desirably be more than the volume of the cavity 170, however, less bone filler may be introduced with varying results. Once the cavity 170 is substantially filled, the continued introduction of bone filler 180 will desirably pressurize the bone filler 180 in the cavity 170 such that the increased pressure will cause at least a portion of the walls of the cavity to move outward, thereby enlarging the cavity 170 and further compressing cancellous bone and/or moving cortical bone. Desirably, introduction of the bone filler 180 will continue until bone filler leak from the vertebral body appears imminent, the cortical bone has regain its pre-fractured position and/or the practitioner determines that sufficient bone filler 180 has been injected into the bone. If desired, the physician can utilize the cavity-forming device to create additional cavities for bone filler, or the shaft 348 can be removed from the vertebral body to completed the procedure.

The bone filler 180 could be any appropriate filling material used in orthopedic surgery, including, but not limited to, allograft or autograft tissue, hydroxyapatite, epoxy, PMMA bone cement, or synthetic bone substitutes such Osteoset® from Wright Medical Technology, medical grade plaster of paris, Skeletal Repair System (SRS®) cement from Norian Corporation, or Collagraft from Zimmer. As bone filler 180 is introduced into the vertebral body 105, the introduction is desirably monitored by x-ray fluoroscopy, or any other appropriate monitoring device or method, to ensure that bone filler 180 does not flow outside of the vertebral body 105. To facilitate visualization, the bone filler 180 may be mixed with a fluoroscopic agent, such as radio opaque barium sulfate. In another embodiment, the bone filler 180 could comprise a mixture of bone cement and a thixotropic material which desirably limits and/or prevents extravazation of the bone cement.

Figure 5I:
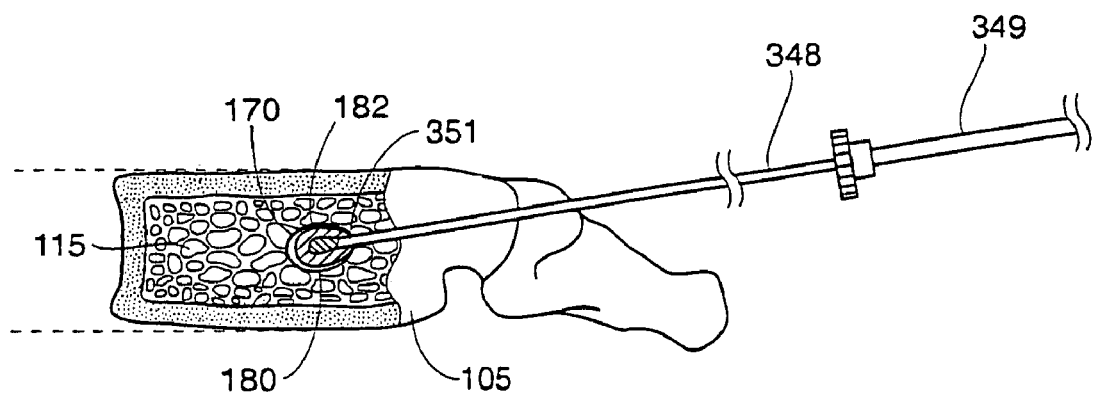
FIG. 5I is a lateral view of the lumbar vertebra of FIG. 5H, with a second bone filler injected into the vertebral body.
Figure 5J:
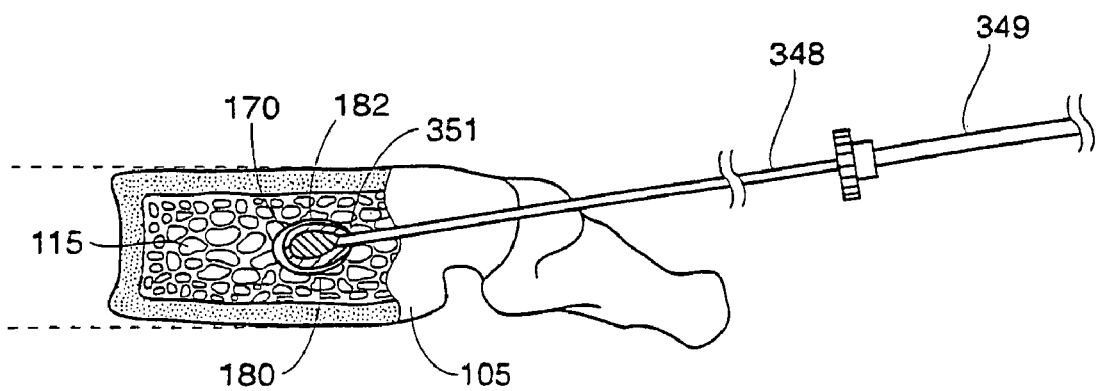
FIG. 5J is a lateral view of the lumbar vertebra of FIG. 5I, with additional bone filler injected into the vertebral body.
Figure 5K:
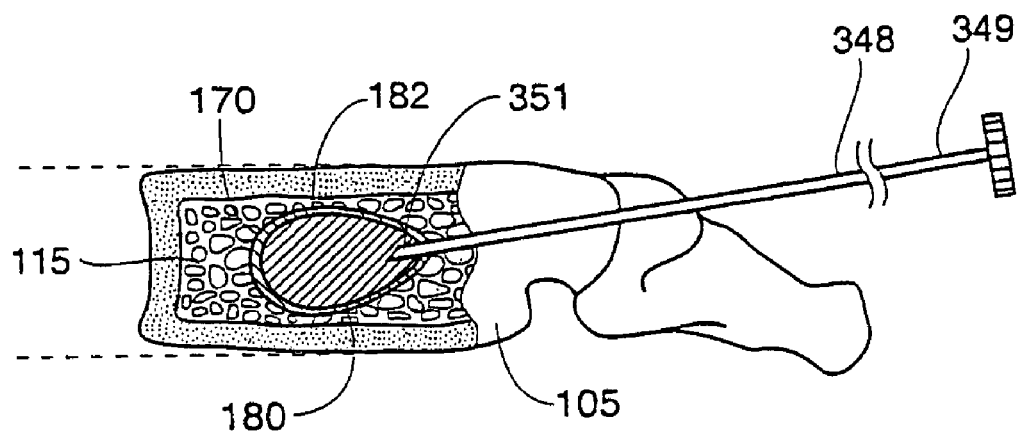
FIG. 5K is a lateral view of the lumbar vertebra of FIG. 5J, with additional bone filler injected into the vertebral body.
Figure 5L:
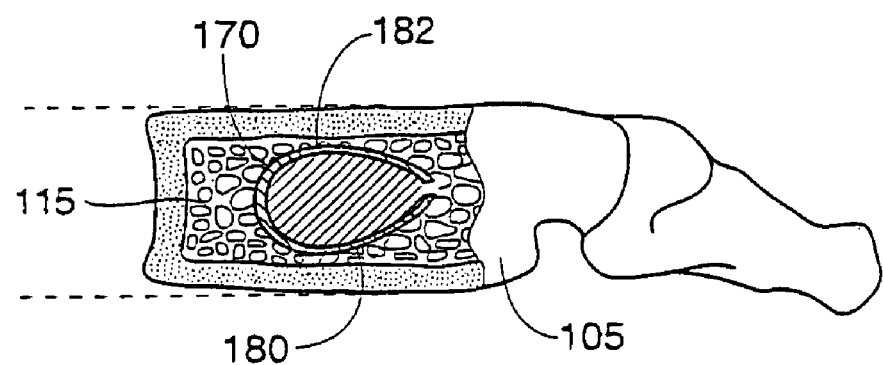
FIG. 5L is a lateral view of the lumbar vertebra of FIG. 5K, with the spinal needle removed from vertebral body.

In an alternate embodiment of the disclosed method, shown in FIGS. 5G through 5L, a first bone filler 180 is introduced into the cavity 170, the amount of first bone filler 180 being desirably less than or approximately equal to the volume of the cavity 170. For example, if the balloon catheter 200 utilized to create the cavity 170 was inflated with 1.0 cc of inflation fluid, then less than or approximately 1.0 cc of bone filler 180 will initially be injected into the cavity 170. Of course, if desired, an amount of first bone filler 180 greater than the cavity volume could be injected into the cavity. The shaft 348 is then repositioned within the vertebral body 105, see FIG. 5H, with the distal end 351 of the device 350 desirably located within the bolus 400 of first bone filler 180 contained in the cavity 170. As best shown in FIG. 5I, a second amount of bone filler 182 is then injected into the vertebral body 105, which desirably forces the first amount of bone filler 180 outward against the walls of the cavity 170. Desirably, the first amount of bone filler 180 will resist extravazating out of the cavity 170 and will push outward against the walls of the cavity 170, further compressing the cancellous bone 115 and/or increasing the size of the cavity 170. Introduction of the second amount of bone filler 182 will desirably continue until bone filler leak from the vertebral body appears imminent, the cortical bone has regained its pre-fractured position, and/or the practitioner determines that sufficient bone filler 180 has been injected into the bone. If desired, the physician could reinsert a catheter 200 to create an additional cavity, or the shaft 348 can be removed to complete the procedure.

Figure 8A:
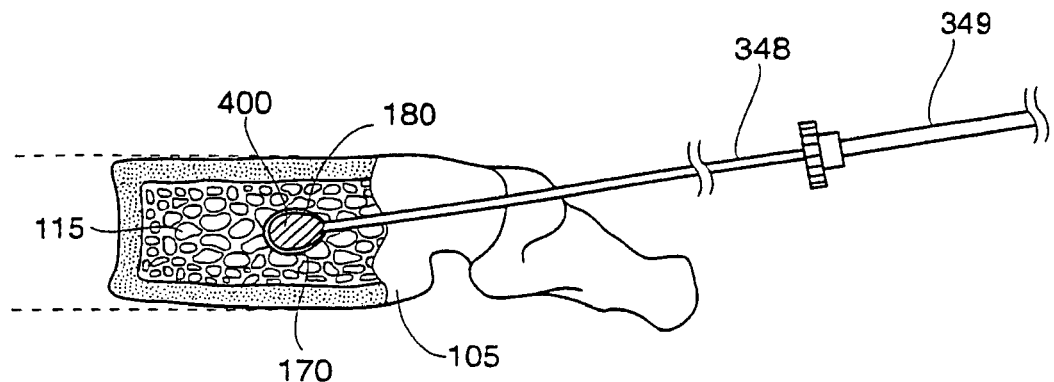
FIG. 8A is a lateral view of a lumbar vertebra, depicting an alternate procedure for treating a vertebral body in accordance with the teachings of the present invention.
Figure 8B:
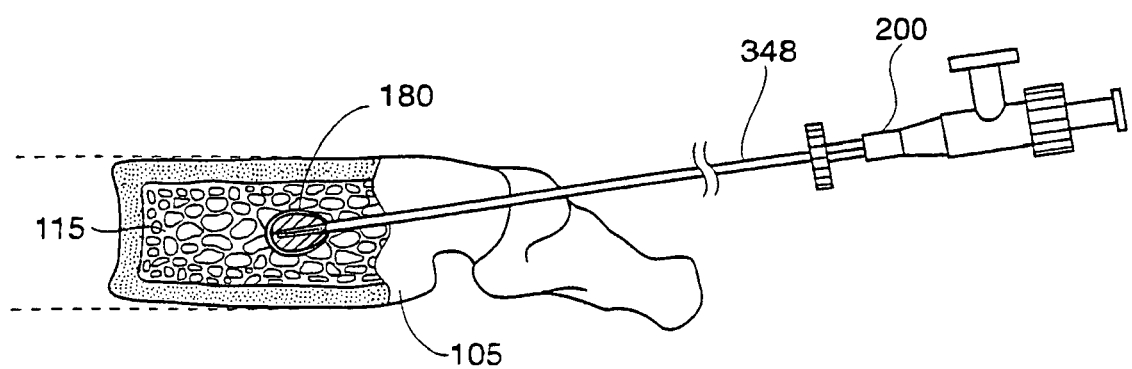
FIG. 8B is a lateral view of the lumbar vertebra of FIG. 8A, with a cavity-forming device inserted into the bone filler.
Figure 8C:
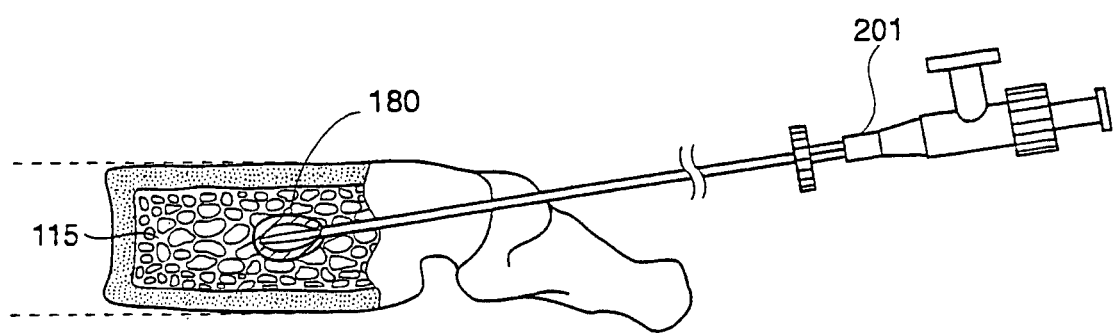
FIG. 8C is a lateral view of the lumbar vertebra of FIG. 8B, with the cavity-forming device expanded in the cavity.

FIGS. 8A through 8C depict an alternate embodiment of the disclosed method, in which the practitioner introduces a first material, such as a bone filler 180, into the cavity 170, and subsequently inserts a cavity-forming device 200 into the bone. The cavity-forming device 200 is then expanded, and desirably compresses the bone filler 180 against the walls of the cavity, sealing any significant cracks and/or venous passages through which the cement will flow. In one further embodiment, a practitioner may wait to allow the first bone filler to harden partially or fully prior to removing the cavity-forming device and/or prior to introducing a second material, such as a bone filler. The second material (not shown) can subsequently be injected into the vertebral body with little fear of leakage. If desired, this method could be utilized whenever cement leakage appears imminent, and can be repeated multiple times until the practitioner determines that sufficient bone filler 180 has been injected into the bone. In addition, the practitioner could repeat this procedure until the cortical bone has regained its pre-fractured position. In an alternate embodiment, the practitioner could utilize a cavity-forming device prior to the introduction of the first bone filler, and then introduce the first bone filler into the cavity, subsequently follow one or more of the described methods.

The first bone filler will desirably comprise a material that can be introduced into the cavity, but which will resist extravazation out of the cavity and/or vertebral body when the second bone filler is injected into the cavity. In one embodiment of the invention, the first and second bone fillers comprise bone cement, with the first bone cement being more resistant to extravazation than the second bone cement. For example, the ingredients of the first bone cement could be specifically tailored such that the first bone cement cures faster than the second bone cement. Alternatively, the first bone cement could be prepared and/or introduced into the vertebral body before the second bone cement, allowing the first bone cement to partially or fully cure before the second bone cement. Alternatively, the curing and/or hardening of the first bone cement could be accelerated (by applying heat, for example) or curing and/or hardening of the second bone cement could be retarded (by cooling, for example). In another embodiment, the first and second bone fillers comprise bone cement, with the first bone cement desirably being more viscous than the second bone cement. In another alternate embodiment, the first bone filler comprises an expandable structure, such as a stent.

In another embodiment, the first bone filler comprises a material more viscous than the second bone filler, the first and second bone fillers comprising different materials. In another embodiment, the first bone filler comprises a material which is more resistant to extravazation into the cancellous bone than the second bone filler. In another embodiment, the first bone filler comprises a material having particles generally larger than particles in the second bone filler. In a further embodiment, the particles of the first bone filler are generally larger than the average pore size within the cancellous bone. In another embodiment, the first bone filler comprises a settable material, such as a two-part polyurethane material or other curable bio-material.

FIGS. 16A through 16D depict an alternate embodiment of the disclosed method, in which a first material, such as a bone filler 180, is initially introduced into the cancellous bone 115 of a human bone, such as a vertebral body 105. An expandable structure 210, such as that found at the distal end of a balloon catheter 200, is subsequently inserted into the vertebral body 105. The expandable structure 210 is then expanded, which displaces the bone filler 180 and/or cancellous bone 115, creating a cavity 170 within the vertebral body 105. In one embodiment, the expansion of the expandable structure 210 forces the bone filler 180 further into the cancellous bone 115, and/or further compresses cancellous bone. To minimize bone filler 180 leakage, the bone filler may be allowed to partially or completely harden prior to expansion of the expandable structure 210. Alternatively, the expandable structure 210 may be expanded, and the bone filler 180 allowed to partially or completely harden around the expandable structure 210. In either case, a second material, optionally additional bone filler, may be introduced into the cavity 170. In one embodiment, the second material is a material which supports the bone in a resting position. This method may be utilized whenever cement leakage appears imminent, and may be repeated multiple times until the practitioner determines that sufficient amounts and varieties of material have been introduced into the bone. Alternatively, the practitioner could halt introduction of filler material when the cortical bone regains or approximates its pre-fractured position.

By creating cavities and/or preferred flow paths within the cancellous bone, the present invention obviates the need for extremely high pressure injection of bone filler into the cancellous bone. If desired, the bone filler could be injected into the bone at or near atmospheric and/or ambient pressures, or at pressures less than approximately 400 pounds per square inch, using bone filler delivery systems such as those described in co-pending U.S. patent application Ser. No. 09/134,323, which is incorporated herein by reference. Thus, more viscous bone fillers (such as, for example, thicker bone cement) can be injected into the bone under low pressures (such as, for example, exiting the delivery device at a delivery pressure at or near ambient or atmospheric pressure), reducing opportunities for cement leakage and/or extravazation outside of the bone.

Cavity-Forming Devices

Figure 11:
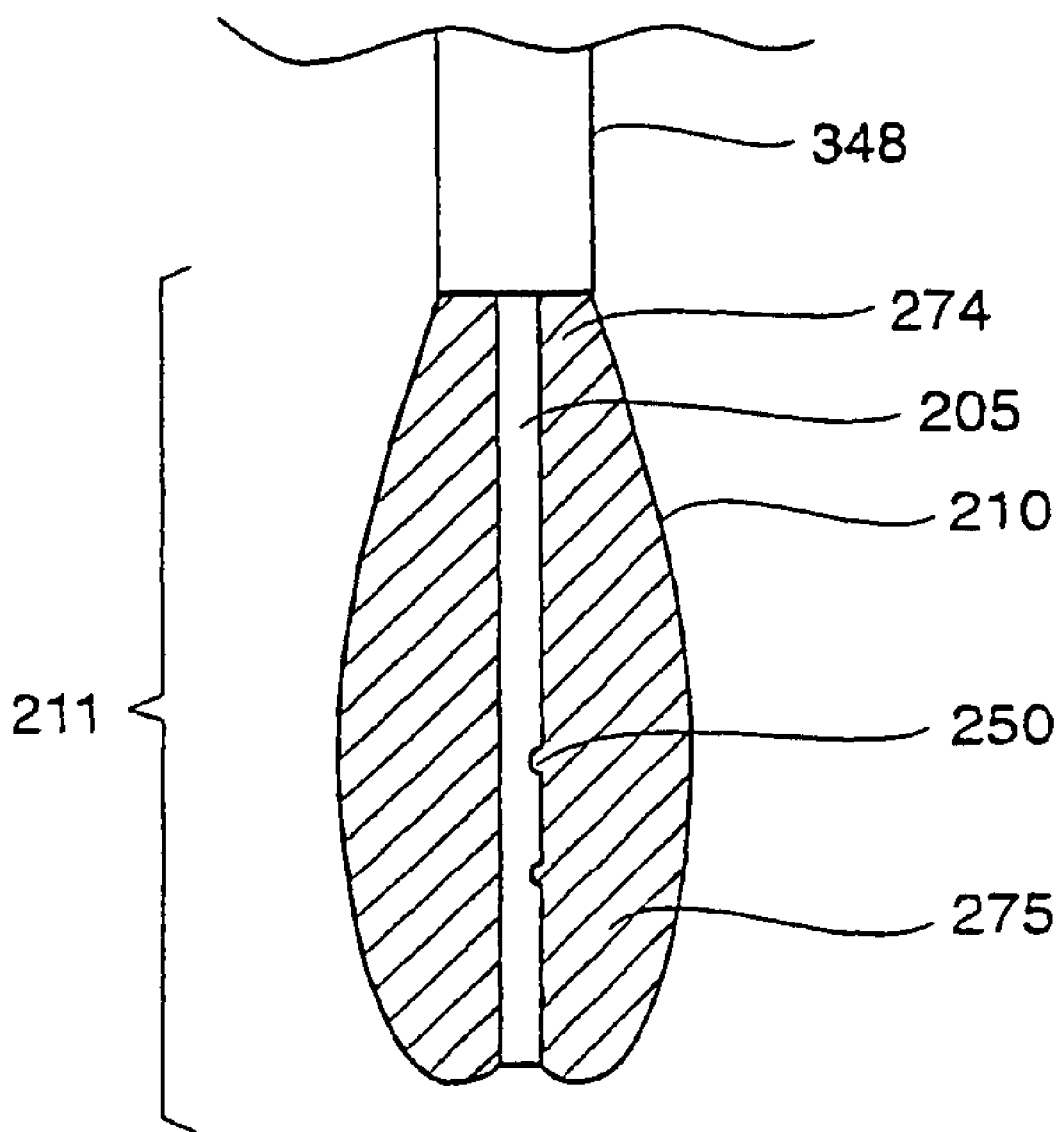
FIG. 11 is a close-up view of the distal end of a balloon catheter protruding from the distal end of a needle, depicting the inflation of the balloon material with an inflation medium.

The present invention also includes cavity-forming devices constructed in accordance with the teachings of the disclosed invention. In one embodiment, the cavity-forming device comprises a balloon catheter 201, as shown in FIGS. 9, 10, and 11. The catheter comprises a hollow tube 205, which is desirably comprised of a medical grade material such as plastic or stainless steel. The distal end 206 of the hollow tube 205 is surrounded by an expandable material 210 comprised of a flexible material such as commonly used for balloon catheters including, but not limited to, metal, plastics, composite materials, polyethylene, mylar, rubber or polyurethane. One or more openings 250 are disposed in the tube 205 near the distal end 206, desirably permitting fluid communication between the hollow interior of the tube 205 and the lumen formed between the tube 205 and the expandable structure 210. A fitting 220, having one or more inflation ports 222, 224, is secured to the proximal end 207 of the tube 205. In this embodiment, once the catheter 201 is in its desired position within the vertebral body 105, an inflation medium 275 is introduced into the fitting 220 through the inflation port 222, where it travels through the fitting 220, through the hollow tube 205, through the opening(s) 250 and into the lumen 274 between the expandable structure 210 and the hollow tube 205. As injection of the inflation medium 275 continues, the pressure of the inflation medium 275 forces the expandable structure 210 away from the hollow tube 205, inflating it outward and thereby compressing cancellous bone 115 and forming a cavity 170. Once a desired cavity size is reached, the inflation medium 275 is withdrawn from the catheter 200, the expandable structure collapses within the cavity 170, and the catheter 200 may be withdrawn.

For example, a balloon catheter 201 constructed in accordance with one preferred embodiment of the present invention, suitable for use with an 11-gauge needle, would comprise a hollow stainless steel hypodermic tube 205, having an outer diameter of 0.035 inches and a length of 10.75 inches. One or more openings 250 are formed approximately 0.25 inches from the distal end of the tube 205. In a preferred embodiment, the distal end 206 of the hollow tube 205 is sealed closed using any means well known in the art, including adhesive (for example, UV 198-M adhesive commercially available from Dymax Corporation—cured for approximately 15 minutes under UV light).

Figure 12:
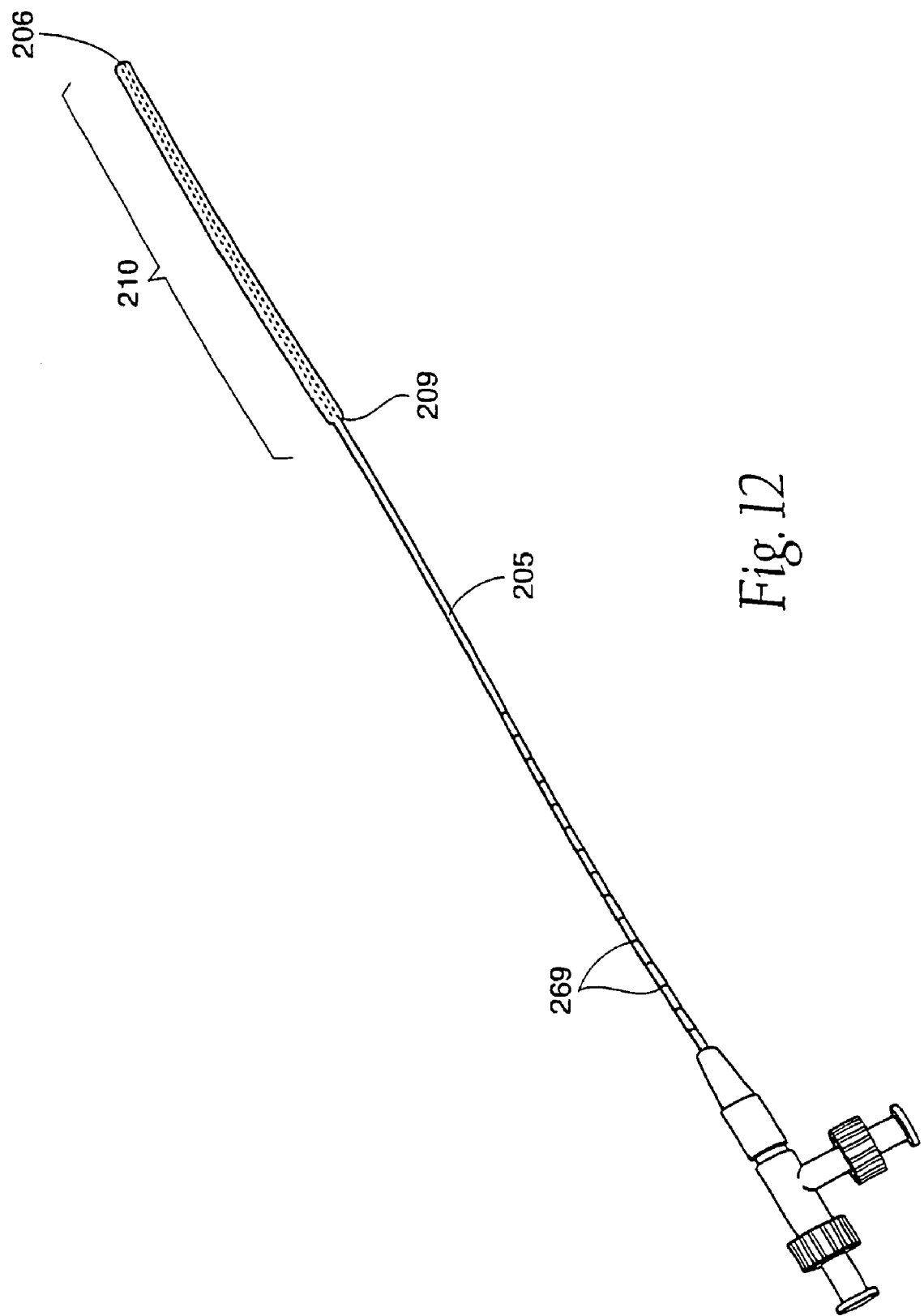
FIG. 12 is a side view of a cavity-forming device constructed in accordance with an alternate embodiment of the present invention.

In one embodiment, the hollow tube 205 is substantially surrounded by an expandable structure 210 comprising an extruded tube of polyurethane (for example, TEXIN® 5290 polyurethane, available commercially from Bayer Corporation). In one embodiment, the polyurethane tube has an inner diameter of 0.046 inches, an outer diameter of 0.082 inches, and a length of 9½ inches. The distal end of the polyurethane tube is bonded to the distal end 206 of the hollow tube 205 by means known in the art, such as by a suitable adhesive (for example, UV 198-M adhesive). Alternatively, the polyurethane tube may be heat sealed about the distal end 206 of the hollow tube 205 by means well known in the art. A ¾ inch long piece of heat shrink tubing 215 (commercially available from Raychem Corporation), having a ³⁄₁₆ inch outer diameter, may be secured around the proximal end of the polyurethane tubing. In one embodiment, the proximal end of the hollow tubing 205 is inserted into the fitting 220 and the heat shrink tubing 215 is desirably bonded into the fitting 220 using a suitable adhesive known in the art, such as UV 198-M. The fitting 220, which may be a Luer T-fitting, commercially available from numerous parts suppliers, may be made of any appropriate material known to those of skill in the art. The fitting 220 comprises one or more ports 222, 224 for attachment to additional instruments, such as pumps and syringes (not shown). If desired, the hollow tube 205 can similarly be bonded into the fitting 220 using a suitable adhesive. Alternatively, as shown in FIG. 12, the expandable structure 210 could be significantly shorter than the hollow tube 205 and be bonded at its distal end 206 and its proximal end 209 to the hollow tube 205.

The hollow tube 205 and one or more openings 250 facilitate the withdrawal of inflation medium from the catheter during the disclosed procedures. When a catheter is deflated, the expandable structure 210 will normally collapse against the tube 205, which can often seal closed the lumen (in the absence of at least one secondary withdrawal path) and inhibit further withdrawal of inflation medium from the expanded structure 210 of a catheter. However, in an embodiment of the disclosed invention, the one or more openings 250 near the distal end of the tube 205 allow inflation medium 275 to be drawn through the hollow hypodermic tube 205, further deflating the expandable structure 210. The strong walls of the hollow hypodermic tube 205 resist collapsing under the vacuum which evacuates the inflation medium, maintaining a flow path for the inflation medium and allowing the inflation medium to be quickly drawn out of the catheter, which desirably permits deflation of the catheter in only a few seconds.

In the disclosed embodiment, as the catheter 201 is inflated, the inflation medium 275 will typically seek to fill the entire lumen between the expandable structure 210 and the hollow tube 205, thus expanding the catheter 201 along the entire length of the expandable structure 210. However, because much of the catheter 201 is located within the lumen of the shaft 348, with the distal end 206 of the catheter 201 extending into the vertebral body 105, the shaft 348 will desirably constrain expansion of the expandable structure 210, causing the expandable structure 210 to expand primarily at the distal end 206 of the catheter 200. Desirably, further insertion or withdrawal of the catheter 201 will alter the amount of the expandable structure 210 extending from the distal end of the shaft 348, thereby increasing or decreasing the length of the expandable structure 210 that is free to expand within the vertebral body 105. By choosing the amount of catheter 201 to insert into the vertebral body 105, the practitioner can alter the length of the expandable structure, and ultimately the size of the cavity 170 created by the catheter 201, during the surgical procedure. Therefore, the disclosed embodiments can obviate and/or reduce the need for multiple catheters of varying lengths. If desired, markings 269 (see FIG. 9) can be placed along the proximal section of the catheter which correspond to the length of the catheter 201 extending from the shaft 348, allowing the practitioner to gauge the size of the expandable structure 210 of the catheter 200 within the vertebral body 105. Similarly, in an alternate embodiment as disclosed below, the cavity-forming device 201 could incorporate markings corresponding to the length of the bristles 425 extending beyond the tip of the shaft 348.

Figure 13:
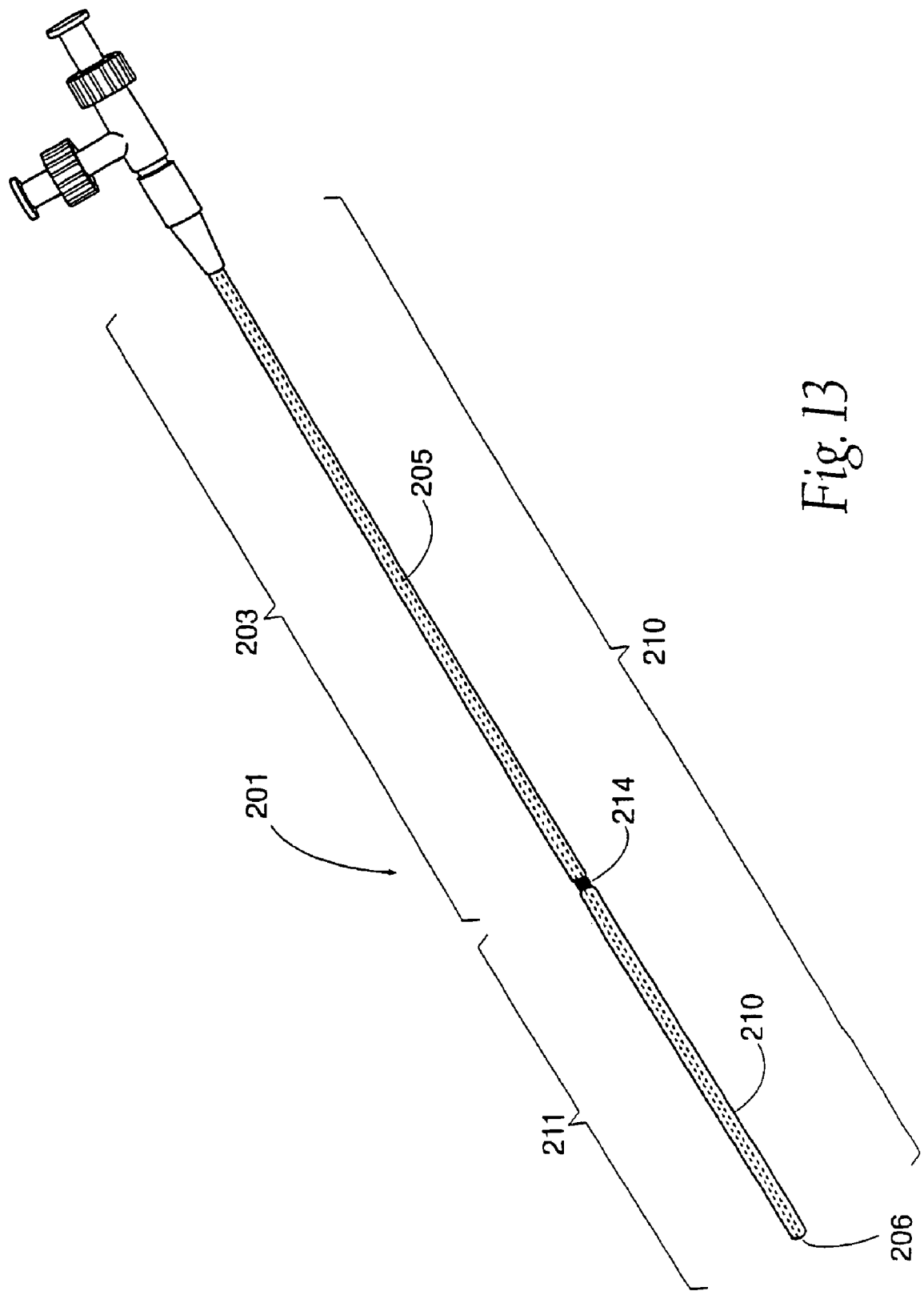
FIG. 13 is a side view of a cavity-forming device constructed in accordance with another alternate embodiment of the present invention.

In an alternate embodiment, shown in FIG. 13, the length of an expandable section 211 of the catheter can be further constrained by securing and/or adhering the expandable structure 210 at a secondary location 214 along the hollow tube 205, thereby limiting expansion beyond the secondary location 214. For example, if a desired maximum length of the expandable section 211 were 3 inches, then the expandable structure 210 could be secured to the hollow tube 205 at a secondary location 214 approximately three inches from the distal end 206 of the hollow tube 205. This arrangement would desirably allow a practitioner to choose an expanded length of the expandable section 211 of up to three inches, while limiting and/or preventing expansion of the remaining section 203 of the catheter 201. This arrangement can also prevent unwanted expansion of the portion 202 of the catheter extending out of the proximal end 191 of the shaft body 348 (see FIG. 5C).

As previously noted, in the disclosed embodiment, the expandable structure is desirably secured to the distal end of the hollow tube, which will facilitate recovery of fragments of the expandable structure 210 if the expandable structure 210 is torn or damaged, such as by a complete radial tear. Because the hollow tube 205 will desirably remain attached to the fragments (not shown) of the expandable structure 210, these fragments can be withdrawn from the vertebral body 105 with the hollow tube 205. In addition, the distal attachment will desirably prevent and/or reduce significant expansion of the expandable structure 210 along the longitudinal axis of the hollow tube 205.

Figure 17:
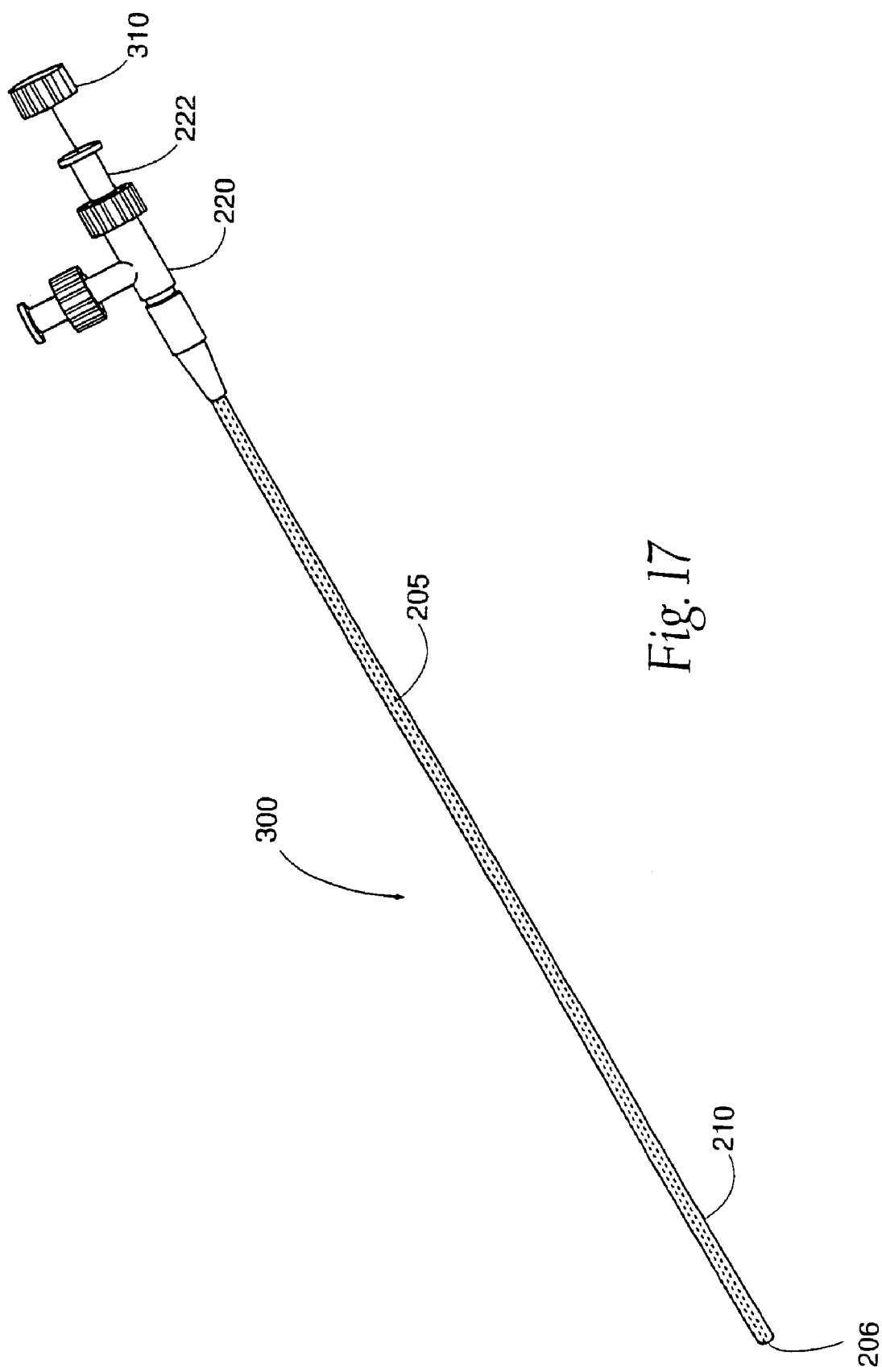
FIG. 17 is a side view of a cavity-forming device constructed in accordance with another alternate embodiment of the present invention.

FIG. 17 depicts a cavity-forming device 300 constructed in accordance with an alternate embodiment of the present invention. Because many of the features of this embodiment are similar to embodiments previously described, like reference numerals will be used to denote like components. In this embodiment, the hollow tube 205 extends through the fitting 220, such as a t-shaped fitting, and is secured to a cap 310. In a preferred embodiment, the hollow tube 205 is capable of rotation relative to the fitting 220. If desired, a seal (not shown), such as a silicone or teflon o-ring, can be incorporated into the proximal fitting 222 to limit and/or prevent leakage of inflation medium past the hollow tube 205.

In use, a cavity-forming device 300 compresses cancellous bone and/or forms a cavity in a manner similar to the embodiments previously described. However, once the cavity is formed and withdrawal of the device 300 is desired, the cap 310 can be rotated, twisting the expandable material 210 relative to the fitting 220 and drawing the expandable structure 210 against the hollow tube 205, desirably minimizing the overall outside diameter of the expandable portion of the device 300. The device 300 can then easily be withdrawn through the shaft 348. Even where the expandable structure 210 has plastically deformed, or has failed in some manner, the present embodiment allows the expandable structure 210 to be wrapped around the hollow tube 205 for ease of withdrawal and/or insertion. Alternatively, the hollow tube 205 may be capable of movement relative to the longitudinal axis of the fitting 220, which would further stretch and/or contract the expandable structure 210 against the hollow tube 205.

Figure 6A:
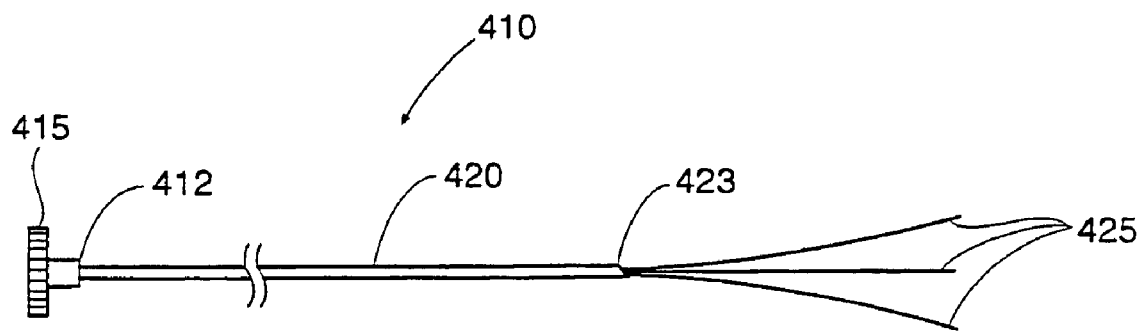
FIG. 6A is a side view of a cavity-forming device constructed in accordance with an alternate embodiment of the present invention.
Figure 6B:
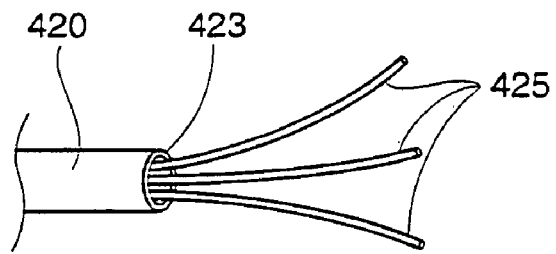
FIG. 6B is a close-up view of the distal end of the cavity-forming device of FIG. 6A.

FIGS. 6A and 6B depict a cavity-forming device 410 constructed in accordance with an alternate embodiment of the present invention. Cavity-forming device 410 comprises a shaft 420 which is desirably sized to pass through the shaft 348 of an insertion device 350. A handle assembly 415, which facilitates manipulation of the cavity-forming device 410, is secured to the proximal end 412 of the shaft 420. One or more wires or "bristles" 425 are secured to the distal end 423 of the shaft 420. The bristles 425 can be secured to the shaft 420 by welding, soldering, adhesives or other securing means well known in the art. Alternatively, the bristle(s) 425 can be formed integrally with the shaft 420, or can be etched from a shaft using a laser or other means well known in the art. The bristles and shaft may be formed of a strong, non-reactive, and medical grade material such as surgical steel. In one embodiment, the bristles 425 extend along the longitudinal axis of the shaft 425, but radiate slightly outward from the shaft axis. In this manner, the bristles 425 can be collected or "bunched" to pass through the shaft 348, but can expand or "fan" upon exiting the shaft 348. If desired, the bristles can be straight or curved, to facilitate passage through the cancellous bone 115. In addition, if desired, one or more of the bristles 425 may be hollow, allowing a practitioner to take a biopsy sample of the cancellous bone during insertion of the device 410.

Figure 7A:
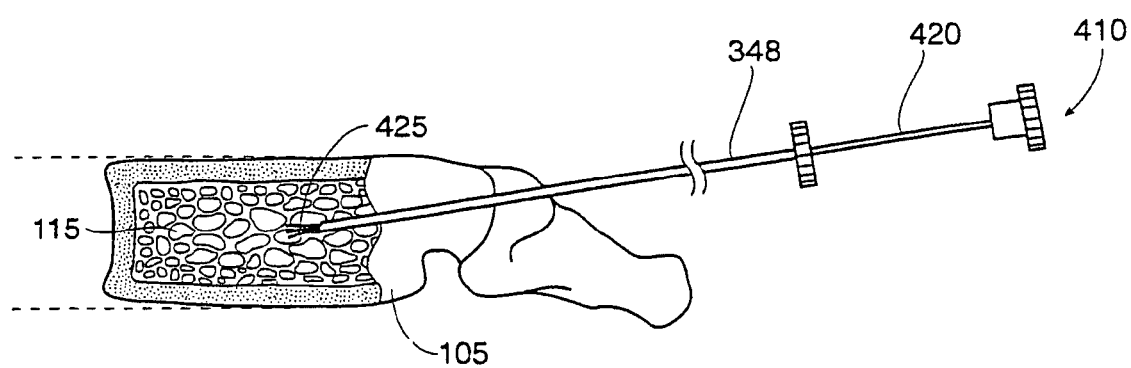
FIG. 7A is a lateral view of a lumbar vertebra, depicting the cavity-forming device of FIG. 6A being inserted into the vertebra.
Figure 7B:
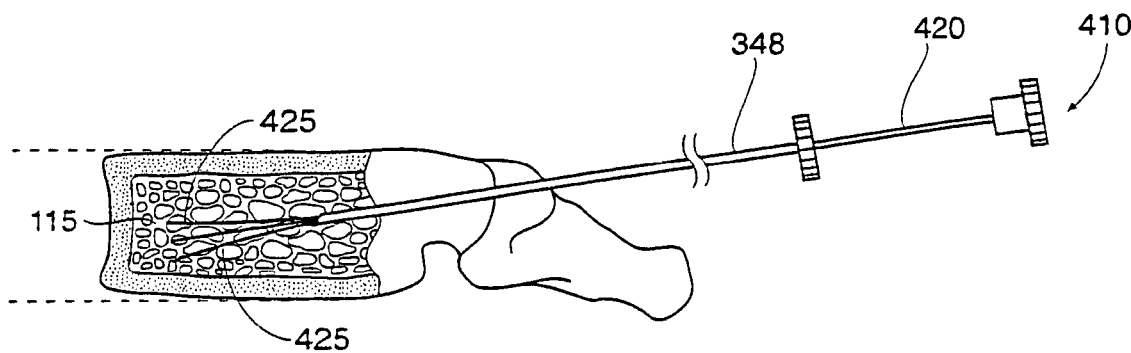
FIG. 7B is a lateral view of the lumbar vertebra of FIG. 7A, with the cavity-forming device deployed within the vertebra.
Figure 7C:
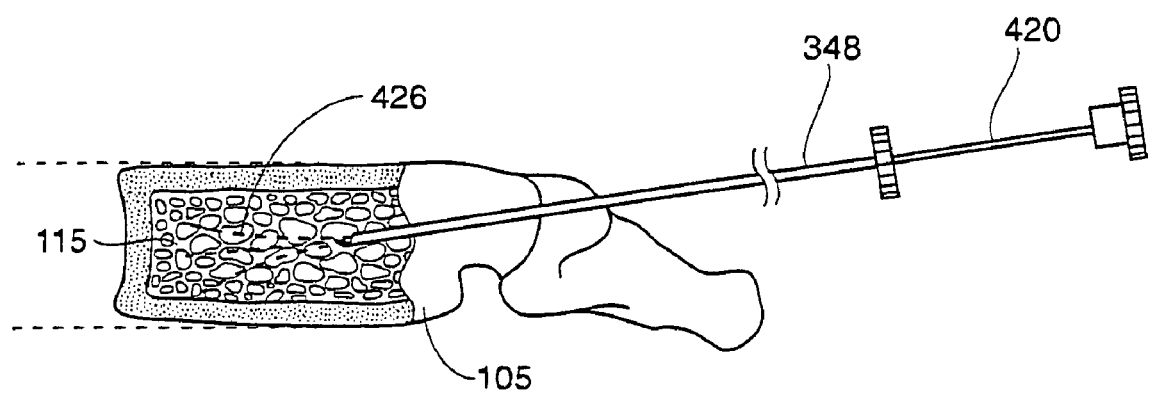
FIG. 7C is a lateral view of the lumbar vertebra of FIG. 7B, with the cavity-forming device withdrawn from the vertebra.

As shown in FIG. 7, the cavity-forming device 410 can desirably be inserted through a shaft 348 positioned in a targeted bone, such as a vertebral body 105. As the bristles 425 enter the cancellous bone 115, the bristles 425 will desirably displace the bone 115 and create one or more cavities 426 or preferred flow paths in the vertebral body. If desired, a practitioner can withdraw the bristles 425 back into the shaft 348, reposition the cavity-forming device 410 (such as by rotating the device 410), and reinsert the bristles 425, thereby creating additional cavities in the cancellous bone 115. After removal of the cavity-forming device 410, a material, such as a bone filler (not shown), may be introduced through the shaft 348. The bone filler will desirably initially travel through the cavities 426 created by the bristles 425. If desired, a practitioner may interrupt introduction of the bone filler and create additional cavities by reinserting the cavity-forming device 410. In addition, in the event bone filler leakage occurs or is imminent, a practitioner can interrupt bone filler injection, create additional cavity(ies) as described above, wait for the introduced/leaking bone filler to harden sufficiently to resist further extravazation, and then continue introduction of bone filler. As previously described, the bone filler could comprise many different materials, or combinations of materials, with varying results.

Figure 14:
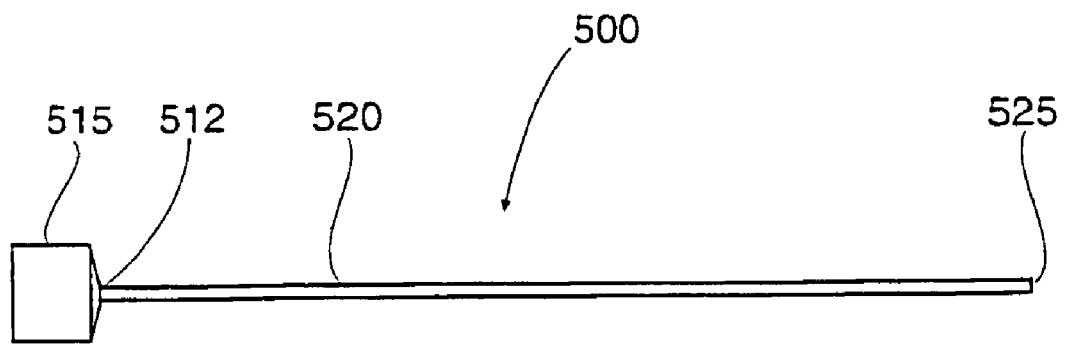
FIG. 14 is a side view of a cavity-forming device constructed in accordance with another alternate embodiment of the present invention.

FIG. 14 depicts a cavity-forming device 500 constructed in accordance with an alternate embodiment of the present invention. The cavity-forming device 500 comprises a shaft 520 which is sized to pass through the shaft 348 of an insertion device 350. A handle assembly 515, which facilitates manipulation of the cavity-forming device 500, is secured to the proximal end 512 of the shaft 520. The shaft 520 of the cavity-forming device 500 is desirably longer than the shaft 348 of the insertion device 350. The distal end 525 of the shaft 520 can be beveled (not shown) to facilitate passage through cancellous bone 115, or can be rounded or flattened to minimize opportunities for penetrating the anterior wall 10 of the vertebral body 105. In addition, if desired, the distal 525 end of the shaft 520 could be hollow (not shown), allowing the practitioner to take a biopsy sample of the cancellous bone 115 during insertion of the device 500.

Figure 15:
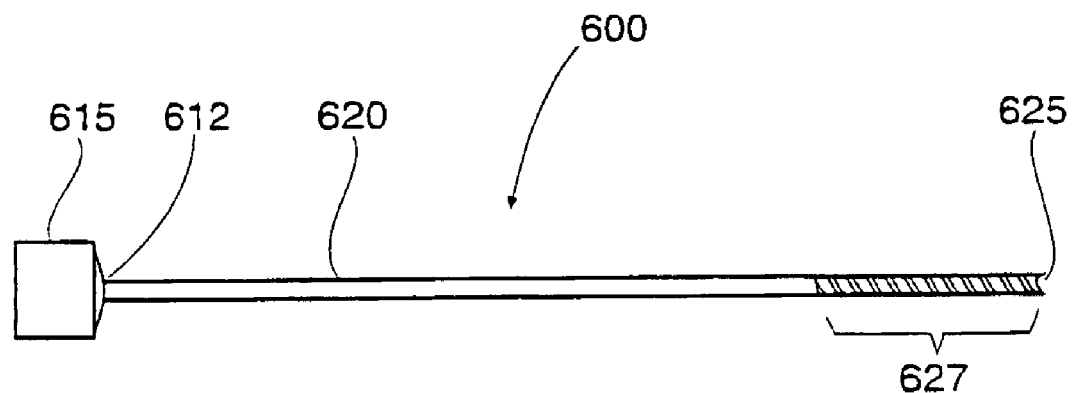
FIG. 15 is a side view of a cavity-forming device constructed in accordance with another alternate embodiment of the present invention.
Figure 16A:
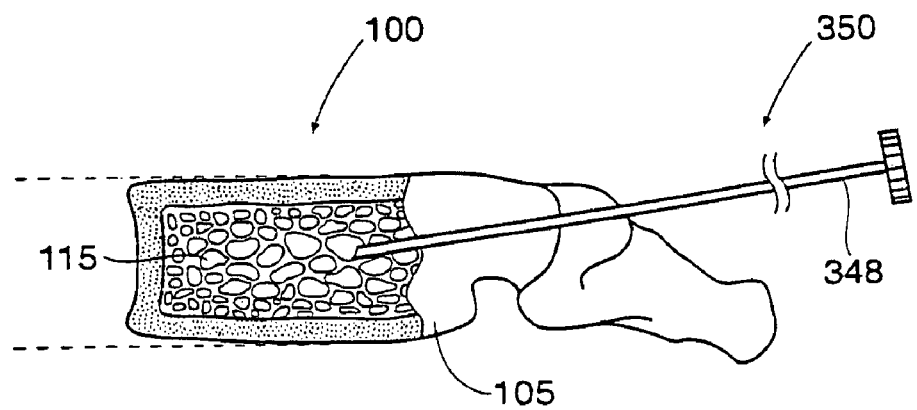
FIG. 16A is a lateral view of a lumbar vertebra, depicting an alternate procedure for treating a vertebral body in accordance with the teachings of the present invention.
Figure 16B:
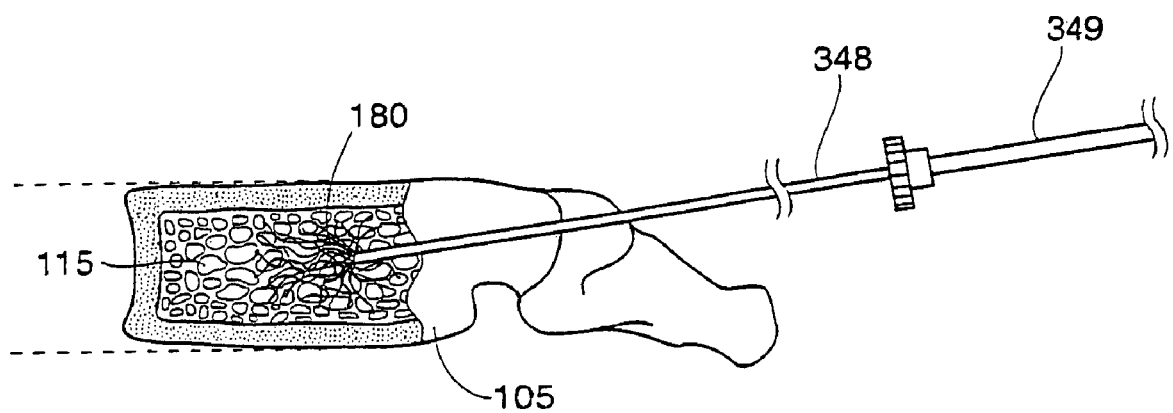
FIG. 16B is a lateral view of the lumbar vertebra of FIG. 16A, with bone filler injected into the vertebra.
Figure 16C:
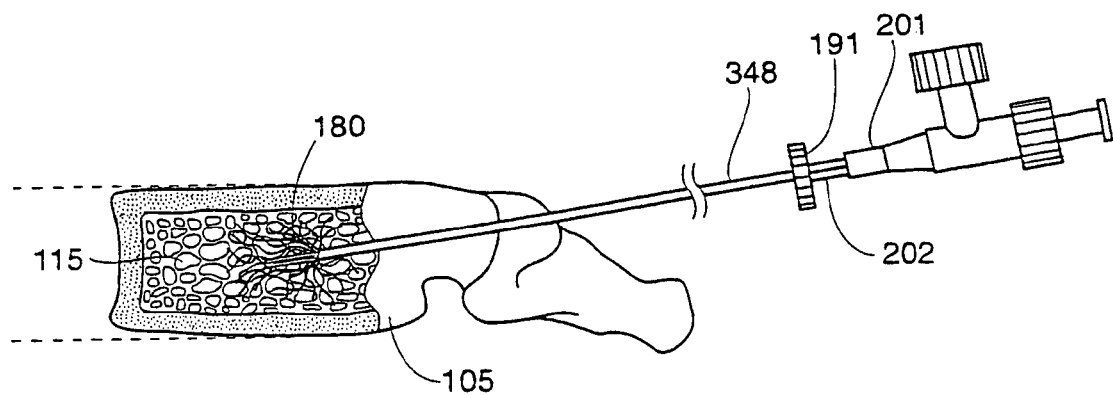
FIG. 16C is a lateral view of the lumbar vertebra of FIG. 16B, with a cavity-forming device inserted into the vertebra.
Figure 16D:
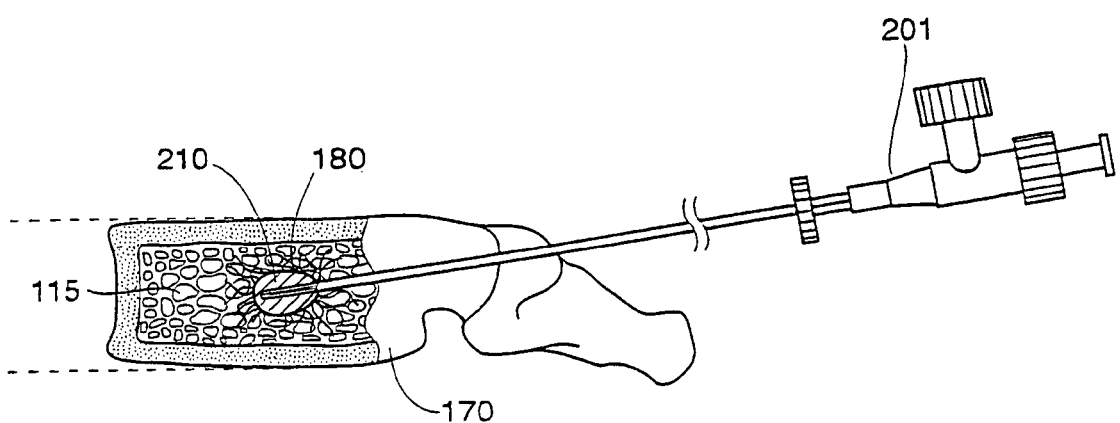
FIG. 16D is a lateral view of the lumbar vertebra of FIG. 16C, with the cavity-forming device expanded in the cavity.

FIG. 15 depicts a cavity-forming device 600 constructed in accordance with an alternate embodiment of the present invention. Cavity-forming device 600 comprises a shaft 620 which is sized to pass through the shaft 348 of an insertion device 350. A handle assembly 615, which facilitates manipulation of the cavity-forming device 600, is secured to the proximal end 612 of the shaft 620. The shaft 620 is desirably longer than the shaft 348 of insertion device 350. The distal end 625 of the shaft 620 can be beveled (not shown) to facilitate passage through cancellous bone 115, or can be rounded or flattened to minimize opportunities for penetrating the anterior wall 10 of the vertebral body 105. In this embodiment, the distal end 625 of the device 600 incorporates drill threads 627 which can facilitate advancement of the device 600 through cancellous bone 115. In addition, if desired, the distal 625 end of the shaft 620 could be hollow, allowing the practitioner to take a biopsy sample of the cancellous bone 115 during insertion of the device 600.

After removal of the device(s), bone filler (not shown) may be introduced through the shaft 348. Desirably, the bone filler will initially travel through the cavity(ies) created by the device(s). If desired, a practitioner can interrupt introduction of bone filler and create additional cavity(ies) by reinserting the device(s). In addition, in the event bone filler leakage occurs or is imminent, the practitioner can interrupt bone filler introduction, create additional cavity(ies) as described above, wait for the introduced/leaking bone filler to harden sufficiently, and then continue introducing bone filler. As previously described, the bone filler could comprise many different materials, or combinations of materials, with varying results.

FIGS. 18-20 depicts a cavity-forming device 600a constructed in accordance with another alternate embodiment of the present invention. Because many of the components of this device are similar to those previously described, similar reference numerals will be used to denote similar components. Cavity-forming device 600a comprises a shaft 620a which is sized to pass through the shaft 348 of an insertion device 350. A handle assembly 615a, which facilitates manipulation of the cavity-forming device 600a, is secured to the proximal end 612a of the shaft 620a. The shaft 620a is desirably longer than the shaft 348 of insertion device 350. The distal end 625a of the shaft 620a can be rounded or beveled to facilitate passage through cancellous bone 115, or can be or flattened to minimize opportunities for penetrating the anterior wall 10 of the vertebral body 105.

An opening or window 700 is desirably formed in the shaft 620a. As shown in FIGS. 19 and 20, an expandable structure 710 is located at least partially within the shaft 620a, desirably at a position adjacent the window 700. Upon introduction of inflation fluid through a lumen extending through the shaft 620a, the expandable structure 710 expands and at least a portion of the expandable structure 710 will extend out of the shaft 620a through the window 700. Desirably, as the structure continues to expand, the expandable structure 710 will "grow" (P1 to P2 to P3 in FIG. 20) through the window 700, thereby compacting cancellous bone, creating a cavity and/or displacing cortical bone. Upon contraction of the expandable structure 710, most of the expandable structure 710 will desirably be drawn back into the shaft 620a for removal of the tool from the vertebral body. In one embodiment, at least a portion of the material comprising the expandable structure 710 will plastically deform as it expands.

The expandable structure 710 may be comprised of a flexible material common in medical device applications, including, but not limited to, plastics, polyethylene, mylar, rubber, nylon, polyurethane, metals or composite materials. Desirably, the shaft 620a will comprise a material that is more resistant to expansion than the material of the expandable structure 710, including, but not limited to, stainless steel, ceramics, composite material and/or rigid plastics. In an alternate embodiment, similar materials for the expandable structure 710 and shaft 620a may be used, but in different thickness and/or amounts, thereby inducing the expandable structure to be more prone to expansion than the shaft 620a material. The expandable structure 710 may be bonded directly to the shaft 620a by various means well known in the art, including, but not limited to, means such as welding, melting, gluing or the like. In alternative embodiments, the expandable structure may be secured inside or outside of the shaft 620a, or a combination thereof.

As previously noted, any of the cavity-forming devices 500, 600 and 600a may be inserted through a shaft 348 positioned in a targeted bone, such as a vertebral body 105. As the device(s) enter the cancellous bone 115, they will desirably displace the bone 115 and create one or more cavities in the vertebral body. If desired, the physician can withdraw the device(s) back into the shaft 348 and reinsert as necessary to create the desired cavity(ies) in the cancellous bone 115.

In the embodiment of a cavity-forming device of FIGS. 18-20, the cavity-forming device 600a may be utilized without an associated insertion device. In such a case, the cavity-forming device desirably will incorporate a sharpened distal tip capable of penetrating the soft tissues and cortical/cancellous bone of the vertebral body. If desired, the distal tip can be hollow or a solid construct. Similarly, the window may extend around more or less of the periphery of the shaft 620a, depending upon the size and configuration of the expandable structure and the desired strength of the cavity-forming device.

By creating one or more cavities within the cancellous bone 115, the cavity-forming devices of the present invention desirably create preferred flow paths for the bone filler 180. In addition, the cavity-forming devices can also desirably close and/or block other natural flow paths out of the cavity, such as veins and/or cracks in the cancellous bone. Moreover, methods and devices disclosed herein can be used to manipulate bone filler already introduced into the bone. Thus, the present invention reduces opportunities for cement leakage outside of the vertebral body and/or improves the distribution of bone filler throughout significant portions of the vertebral body. In addition, the creation of cavities and desired flow paths described in the present invention permits the placement of biomaterial more safely, under greater control and under lower pressures.

In addition to the specific uses described above, the cavity-forming devices and methods described herein would also be well-suited for use in treating and/or reinforcing weakened, diseased and/or fractured bones and other organs in various locations throughout the body. For example, the disclosed devices and methods could be used to deliver reinforcing materials and/or medications, such as cancer drugs, replacement bone cells, collagen, bone matrix, demineralized calcium, and other materials/medications, directly to a fractured, weakened and/or diseased bone, thereby increasing the efficacy of the materials, reinforcing the weakened bone and/or speed healing. Moreover, injection of such materials into one bone within a body could permit the medication/material to migrate and/or be transported to other bones and/or organs in the body, thereby improving the quality of bones and/or other organs not directly injected with the materials and/or medications.

Other embodiments and uses of the invention will be apparent to those skilled in the art from consideration of the specification and practice of the invention disclosed herein. All documents referenced herein are specifically and entirely incorporated by reference. The specification and examples should be considered exemplary only with the true scope and spirit of the invention indicated by the following claims. As will be easily understood by those of ordinary skill in the art, variations and modifications of each of the disclosed embodiments can be easily made within the scope of the claims.

We claim:

1. A method comprising
establishing a percutaneous path into a vertebral body having cortical bone enclosing a cancellous bone volume,
forming a cavity in the cancellous bone volume,
compressing at least a portion of the cancellous bone volume by injecting a pressurized flowable bone filler material directly into the cavity,
pushing the flowable bone filler material outward against the walls of the cavity to increase the size of the cavity by injecting additional flowable bone filler material into the cavity; and
moving a fractured cortical bone of the vertebral body to a pre-fractured position by injecting additional flowable bone filler material into the cavity.

2. A method according to claim 1, wherein the flowable bone filler material comprises a bone cement.

3. A method according to claim 1, wherein the bone filler material comprises a bone cement.

4. A method of claim 1, wherein the flowable bone filler material comprises a bone cement.

5. A method comprising establishing a percutaneous path into a bone structure having cortical bone enclosing a cancellous bone volume, introducing a flowable bone filler material directly into at least a portion of the cancellous bone volume, pressurizing the flowable bone filler material within the bone structure by continuing the introduction of the flowable bone filler material into the cancellous bone volume, compressing the cancellous bone volume within the bone structure by the pressurizing of the flowable bone filler material; and moving a fractured cortical bone of the vertebral body to a pre-fractured position by injecting additional flowable bone filler material into the cavity.

6. A method according to claim 5 wherein the pressurizing of the flowable bone filler material within the bone structure moves fractured cortical bone.

7. A method according to claim 5 wherein the bone structure comprises a vertebral body.

8. A method according to claim 5 wherein the flowable bone filler material comprises a bone cement.

9. A method according to claim 5, wherein the flowable bone filler material comprises at least one of a bone filler, a bone cement, a synthetic bone substitute, a bone biomaterial, a hydroxyapatite material, a bone mineral material, a thixotropic material, a curable biomaterial, allograft tissue, and autograft tissue.

10. A method comprising creating a cavity a vertebral body, introducing a first amount of a flowable bone filler material directly into the cavity, introducing a second amount of pressurized flowable bone filler material into the cavity such that the flowable bone filler material pushes outward against a wall of the cavity, thereby compressing a cancellous bone in the vertebral body and increasing the size of the cavity; and moving the cortical bone until the fractured cortical bone regains a pre-fractured position.

11. A method according to claim 9 wherein introducing the second amount of the flowable bone filler material moves fractured cortical bone of the vertebral body.

12. A method comprising compressing at least a portion of a cancellous bone volume within a vertebral body by injecting a flowable bone filler material directly into the cancellous bone volume, moving fractured cortical bone of the vertebral body by injecting pressurized flowable bone filler material into the vertebral body, comprising moving fractured cortical bone to a pre-fractured position.

13. A method according to claim 12 wherein the flowable bone filler comprises a bone cement.

14. A method according to claim 12, wherein the flowable bone filler material comprises at least one of a bone filler, a bone cement, a synthetic bone substitute, a bone biomaterial, a hydroxyapatite material, a bone mineral material, a thixotropic material, a curable biomaterial, allograft tissue, and autograft tissue.

* * * * *